US009683259B2

(12) United States Patent
Chun et al.

(10) Patent No.: US 9,683,259 B2
(45) Date of Patent: Jun. 20, 2017

(54) DETECTION OF TARGET NUCLEIC ACID SEQUENCE BY PTO CLEAVAGE AND EXTENSION-DEPENDENT SIGNALING OLIGONUCLEOTIDE CLEAVAGE

(71) Applicants: Jong Yoon Chun, Seoul (KR); Young Jo Lee, Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 136 days.

(21) Appl. No.: 14/394,780

(22) PCT Filed: Apr. 16, 2013

(86) PCT No.: PCT/KR2013/003196
§ 371 (c)(1),
(2) Date: Oct. 16, 2014

(87) PCT Pub. No.: WO2013/157821
PCT Pub. Date: Oct. 24, 2013

(65) Prior Publication Data
US 2015/0167060 A1 Jun. 18, 2015

(30) Foreign Application Priority Data
Apr. 19, 2012 (KR) .................. 10-2012-0040864

(51) Int. Cl.
C12Q 1/68 (2006.01)
C12Q 1/34 (2006.01)
(52) U.S. Cl.
CPC ......... *C12Q 1/6823* (2013.01); *C12Q 1/6818* (2013.01); *C12Q 1/34* (2013.01)
(58) Field of Classification Search
None
See application file for complete search history.

(56) References Cited

U.S. PATENT DOCUMENTS

| 2006/0040282 A1 | 2/2006 | Monforte et al. |
| 2009/0023151 A1 | 1/2009 | Dawson et al. |
| 2009/0305237 A1 | 12/2009 | Cantor et al. |
| 2010/0129812 A1 | 5/2010 | Yoo |

FOREIGN PATENT DOCUMENTS

| EP | 0878554 A2 | 11/1998 |
| JP | 2003334097 A | 11/2003 |
| JP | 2008519605 A | 12/2008 |
| WO | 2009155271 A1 | 12/2009 |
| WO | 2011027966 A2 | 3/2011 |
| WO | 2011028041 A2 | 3/2011 |
| WO | 2011037306 A1 | 3/2011 |
| WO | 2011078441 A1 | 6/2011 |
| WO | 2013115442 A1 | 8/2013 |

OTHER PUBLICATIONS

Allawi, H., et al.; Quantitation of microRNAs using a modified Invador assay; RNA Society, vol. 10, 2004, pp. 1153-1161.
Olivier, M.; The invader assay of SNP genotyping Elsevier, Mutation Research, vol. 573, 2005, pp. 103-110.
Lyamichev, V et al.; Polymorphism identification and quantitative detection of genomic DNA by invasive cleavage of oligonucleotide probes; 1999 Nature America Inc., Nature Biotechnology, vol. 17, Mar. 1999, pp. 292-296.

*Primary Examiner* — James Martinell
(74) *Attorney, Agent, or Firm* — Gianna J. Arnold; Saul Ewing LLP

(57) ABSTRACT

The present invention relates to the detection of a target nucleic acid sequence by a PTO Cleavage and Extension-Dependent Signaling Oligonucleotide Cleavage assay (PCE-SC assay). The present invention is carried out in such a manner that the extended strand is produced on the CTO having arbitrary sequences as templates depending on the presence of target nucleic acid sequences and in turn the SO as probes is hybridized with the extended strand to give signal. The present invention employs a series of reactions including PTO hybridization and cleavage, CTO hybridization and extension, and SO hybridization and cleavage, which is responsible for the highly enhanced specificity of the present invention.

22 Claims, 10 Drawing Sheets

A. Probing and Tagging Oligonucleotide (PTO)

B. Capturing and Templating Oligonucleotide (CTO)

C. Signaling Oligonucleotide (SO)

A. Hybridization

B. Primer extension & Cleavage of PTO

C. Hybridization of PTO fragment to CTO and Extension

D. Hybridization of SO to extended strand

E. Cleavage of SO by 5' nuclease, ribonuclease or restriction enzyme & Detection

A. Hybridization

B. Primer extension & Cleavage of PTO

C. Hybridization of PTO fragment to CTO and Extension

D. Hybridization of SO and UO to extended strand

E. Cleavage of SO by 5' nuclease & Detection

A. Hybridization

B. Primer extension & Cleavage of PTO

C. Hybridization of PTO fragment to CTO and Extension

D. Hybridization of SO and UO to extended strand

E. Cleavage of SO by 5' nuclease & Detection

A. Hybridization

B. Primer extension & Cleavage of PTO

C. Hybridization of PTO fragment to CTO and Extension

D. Hybridization of SO and UO to extended strand

E. Cleavage of SO by 5' nuclease & Detection

A. Hybridization

B. Primer extension & Cleavage of PTO

C. Hybridization of PTO fragment to CTO and Extension

D. Hybridization of SO to extended strand

E. Cleavage of SO by 5' nuclease, ribonuclease or restriction enzyme & Detection

Fig. 7

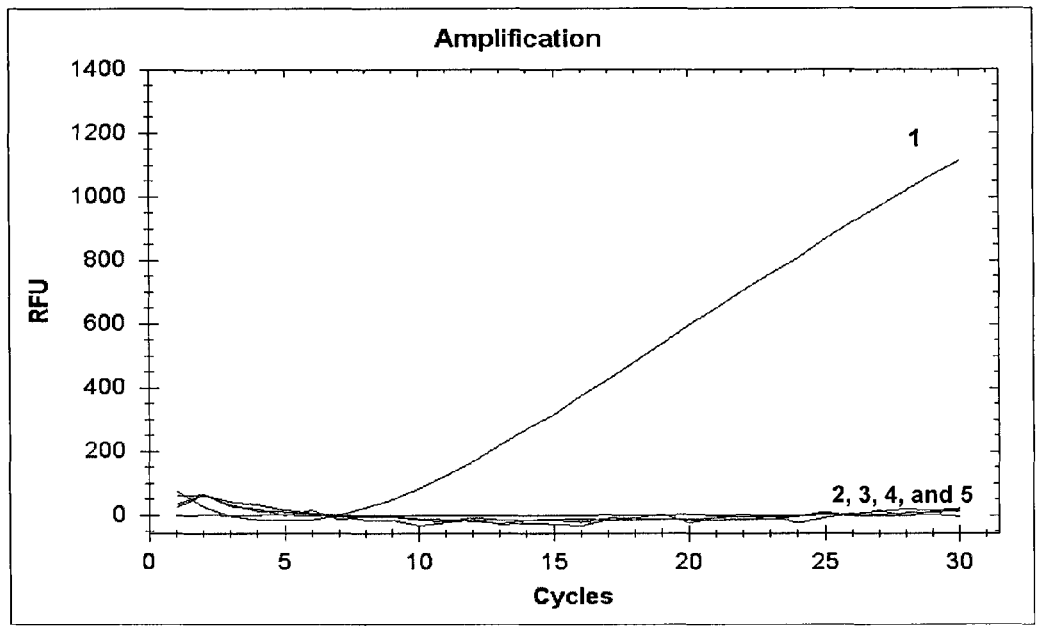

| No. | Template [1] | Upstream Primer [2] | PTO [3] | CTO [4] | SO [5] |
|---|---|---|---|---|---|
| 1 | + | + | + | + | + |
| 2 | - | + | + | + | + |
| 3 | + | + | - | + | + |
| 4 | + | + | + | - | + |
| 5 | + | + | + | + | - |

[1] Template is a synthetic oligonucleotide for *Neisseria gonorrhoeae*.
[2] Upstream primer is located upstream of PTO.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] SO (Signaling Oligonucleotide) has a fluorescent molecule at its 5'-end and a quencher molecule at its 3'-end.

Fig. 8

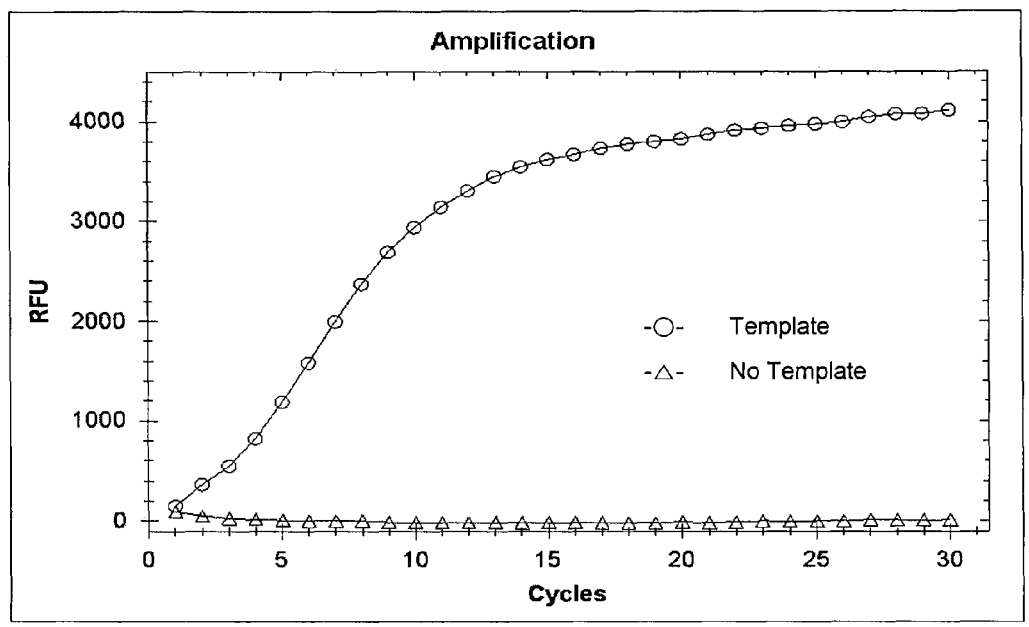

| Template [1] | Upstream Primer [2] | PTO [3] | CTO [4] | SO [5] | UO [6] |
|---|---|---|---|---|---|
| + | + | + | + | + | + |
| − | + | + | + | + | + |

[1] Template is a synthetic oligonucleotide for *Neisseria gonorrhoeae*.
[2] Upstream primer is located upstream of PTO.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] SO (Signaling Oligonucleotide) has a fluorescent molecule at its 5'-end and a quencher molecule at its 3'-end.
[6] UO (Upstream Oligonucleotide) is located upstream of SO.

Fig. 9

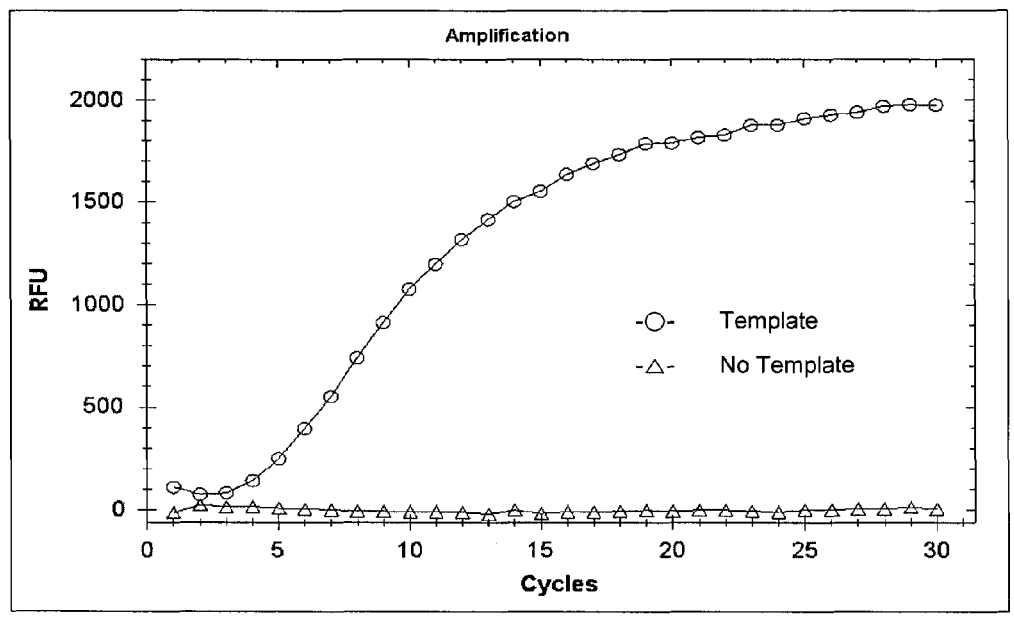

| Template [1] | Upstream Primer [2] | PTO [3] | CTO [4] | SO [5] | UO [6] |
|---|---|---|---|---|---|
| + | - | + | + | + | + |
| - | - | + | + | + | + |

[1] Template is a synthetic oligonucleotide for *Neisseria gonorrhoeae*.
[2] Upstream primer is located upstream of PTO.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] SO (Signaling Oligonucleotide) has a fluorescent molecule at its 5'-end and a quencher molecule at its 3' end.
[6] UO (Upstream Oligonucleotide) is located upstream of SO.

Fig. 10

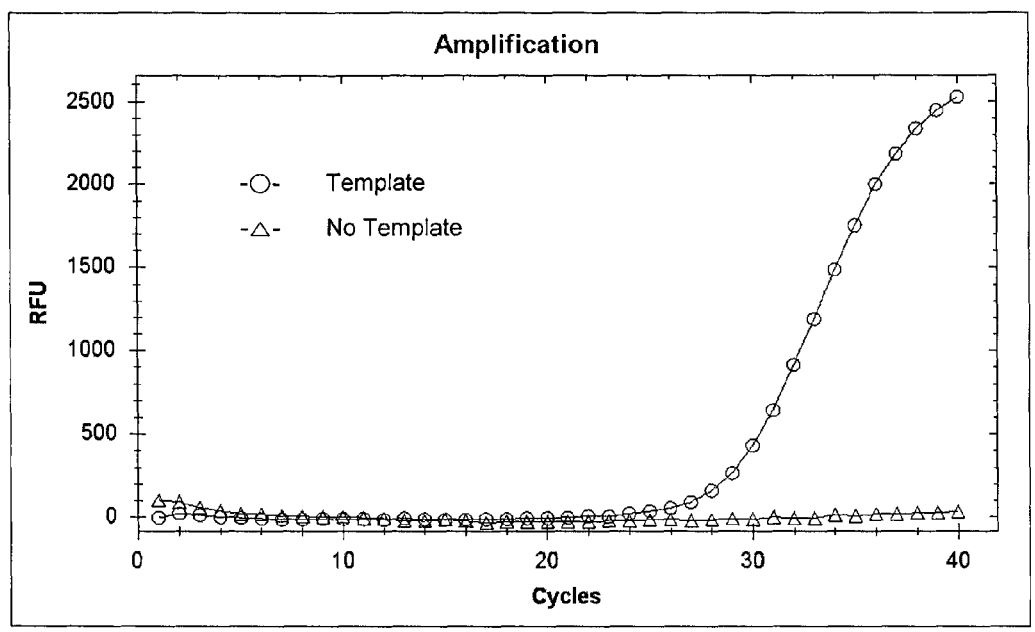

| Template [1] | Primers [2] | PTO [3] | CTO [4] | SO [5] | UO [6] | Ct |
|---|---|---|---|---|---|---|
| + | + | + | + | + | + | 28.51 |
| - | + | + | + | + | + | - |

[1] Template is a genomic DNA of *Neisseria gonorrhoeae*.
[2] Primers are an upstream primer and a downstream primer.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] SO (Signaling Oligonucleotide) has a fluorescent molecule at its 5'-end and a quencher molecule at its 3'-end.
[6] UO (Upstream Oligonucleotide) is located upstream of SO.

SEQUENCE LISTING

<160> NUMBER OF SEQ ID NOS: 7

<210> SEQ ID NO 1
<211> LENGTH: 86
<212> TYPE: DNA
<213> ORGANISM: Artificial Sequence
<220> FEATURE:
<223> OTHER INFORMATION: Synthetic construct; NG-T

<400> SEQUENCE: 1
aaatatgcga aacacgccaa tgaggggcat gatgctttct ttttgttctt gctcggcaga        60
gcgagtgata ccgatccatt gaaaaa        86

<210> SEQ ID NO 2
<211> LENGTH: 21
<212> TYPE: DNA
<213> ORGANISM: Artificial Sequence
<220> FEATURE:

```
<223> OTHER INFORMATION: Synthetic construct; NG-R

<400> SEQUENCE: 2
caatggatcg gtatcactcg c                                              21

<210> SEQ ID NO 3
<211> LENGTH: 35
<212> TYPE: DNA
<213> ORGANISM: Artificial Sequence
<220> FEATURE:
<223> OTHER INFORMATION: Synthetic construct; NG-PTO

<400> SEQUENCE: 3
acgacggctt ggctgcccct cattggcgtg tttcg                               35

<210> SEQ ID NO 4
<211> LENGTH: 71
<212> TYPE: DNA
<213> ORGANISM: Artificial Sequence
<220> FEATURE:
<223> OTHER INFORMATION: Synthetic construct; NG-CTO

<400> SEQUENCE: 4
gtcgtaccga gatgcgcttc tgattcgtgc gctggatacc ctgacgatat ccagccaagc    60
cgtcgtgctg t                                                         71

<210> SEQ ID NO 5
<211> LENGTH: 25
<212> TYPE: DNA
<213> ORGANISM: Artificial Sequence
<220> FEATURE:
<223> OTHER INFORMATION: Synthetic construct; NG-SO

<400> SEQUENCE: 5
tgcgctggat accctgacga tatcc                                          25

<210> SEQ ID NO 6
<211> LENGTH: 18
<212> TYPE: DNA
<213> ORGANISM: Artificial Sequence
<220> FEATURE:
<223> OTHER INFORMATION: Synthetic construct; UO

<400> SEQUENCE: 6
taccgagatg cgcttctg                                                  18

<210> SEQ ID NO 7
<211> LENGTH: 21
<212> TYPE: DNA
<213> ORGANISM: Artificial Sequence
<220> FEATURE:
<223> OTHER INFORMATION: Synthetic construct; NG-F

<400> SEQUENCE: 7
tacgcctgct actttcacgc t                                              21
```

DETECTION OF TARGET NUCLEIC ACID SEQUENCE BY PTO CLEAVAGE AND EXTENSION-DEPENDENT SIGNALING OLIGONUCLEOTIDE CLEAVAGE

CROSS-REFERENCE TO RELATED APPLICATIONS

This application claims the priority of PCT/KR2013/003196, filed on Apr. 16, 2013, which claims priority to Korean Patent Application No. 10-2012-0040864, filed Apr. 19, 2012, the entire contents of each of which are hereby incorporated in total by reference.

SEQUENCE LISTING

This application incorporates by reference the Sequence Listing contained in an ASCII text file named "14_394780_ST25.txt" submitted via EFS-Web. The text file was created on Feb. 23, 2015, and is 2 kb in size

BACKGROUND OF THE INVENTION

Field of the Invention

The present invention relates to the detection of a target nucleic acid sequence by a PTO Cleavage and Extension-Dependent Signaling Oligonucleotide Cleavage assay (PCE-SC assay).

Description of the Related Art

DNA hybridization is a fundamental process in molecular biology and is affected by ionic strength, base composition, length of fragment to which the nucleic acid has been reduced, the degree of mismatching, and the presence of denaturing agents.

DNA hybridization-based technologies would be a very useful tool in specific nucleic acid sequence determination and clearly be valuable in clinical diagnosis, genetic research, and forensic laboratory analysis. However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected. U.S. Pat. No. 7,309,573 disclose a method including formation of a released flap produced by a nucleic acid synthesis; extension of the released flap; cleavage of an oligonucleotide during extension of the flap; and detection of a signal generated by the cleavage of the oligonucleotide.

By hybridization of fluorescence-labeled probes in a liquid phase, a plurality of target nucleic acid sequences may be simultaneously detected using even a single type of a fluorescent label by melting curve analysis. However, the conventional technologies for detection of target sequences by 5' nuclease-mediated cleavage of interactive-dual labeled probes require different types of fluorescent labels for different target sequences in multiplex target detection, which limits the number of target sequences to be detected due to limitation of the number of types of fluorescent labels.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, preferably multiple target sequences, in a liquid phase and on a solid phase by not only hybridization but also enzymatic reactions such as 5' nucleolytic reaction in a more convenient, reliable and reproducible manner. Furthermore, a novel target detection method not limited by the number of types of labels (particularly, fluorescent labels) is also needed in the art.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences, in which target detection is accomplished using enzymatic reactions such as 5' nucleolytic reaction and extension, and extension-dependent hybridization and cleavage reactions as well as probe hybridization, contributing to improvements in the target specificity, process convenience and workability in multiplex detection.

Accordingly, it is an object of this invention to provide a method for detecting a target nucleic acid sequence from a DNA or a mixture of nucleic acids by a PCE-SC (PTO Cleavage and Extension-Dependent Signaling Oligonucleotide Cleavage) assay.

It is another object of this invention to provide a kit for detecting a target nucleic acid sequence from a DNA or a mixture of nucleic acids by a PCE-SC (PTO Cleavage and Extension-Dependent Signaling Oligonucleotide Cleavage) assay.

Other objects and advantages of the present invention will become apparent from the detailed description to follow taken in conjugation with the appended claims and drawings.

BRIEF DESCRIPTION OF THE DRAWINGS

FIG. 2A illustrates hybridization, FIG. 2B illustrates primer extension and cleavage of PTO, FIG. 2C illustrates hybridization of PTO fragment to CTO and extension, FIG. 2D illustrates hybridization of SO to extended strand, and FIG. 2E illustrates cleavage of SO by 5' nuclease, ribonuclease or restriction enzyme and detection. The SO has a reporter molecule and a quencher molecule and is cleaved by 5' nuclease, ribonuclease, or restriction enzyme.

FIG. 3A illustrates hybridization, FIG. 3B illustrates primer extension and cleavage of PTO, FIG. 3C illustrates hybridization of PTO fragment to CTO and extension, FIG. 3D: illustrates hybridization of SO and UO to extended strand, and FIG. 3E illustrates cleavage of SO by 5' nuclease & detection. The SO has a reporter molecule and a quencher molecule and is cleaved by upstream probe-dependent 5' nuclease activity.

FIG. 4A illustrates hybridization, FIG. 4B illustrates primer extension and cleavage of PTO, FIG. 4C illustrates hybridization of PTO fragment to CTO and extension, FIG. 4D illustrates hybridization of SO and UO to extended strand, and FIG. 4E illustrates cleavage of SO by 5' nuclease and detection. The SO has a reporter molecule and a quencher molecule and is cleaved by upstream primer-dependent 5' nuclease activity.

FIG. 5A illustrates hybridization, FIG. 5B illustrates primer extension and cleavage of PTO, FIG. 5C illustrates hybridization of PTO fragment to CTO and extension, FIG. 5D illustrates hybridization of SO and UO to extended strand, and FIG. 5E illustrates cleavage of SO by 5' nuclease and detection. The SO labeled with a reporter molecule and a quencher molecule has a 5'-tagging portion comprising a non-complementary sequence to the extended strand.

FIG. 6A illustrates hybridization, FIG. 6B illustrates primer extension & cleavage of PTO, FIG. 6C illustrates hybridization of PTO fragment to CTO and extension, FIG. 6D illustrates hybridization of SO to extended strand, and FIG. 6E illustrates cleavage of SO by 5' nuclease, ribonuclease or restriction enzyme and Detection. The SO labeled with a single label is immobilized onto a solid substrate via its 3'-end. The SO is cleaved by 5' nuclease, ribonuclease, or restriction enzyme.

FIG. 7 shows the results of the detection of *Neisseria gonorrhoeae* gene by PCE-SC assay using an upstream primer to the PO. The SO has a reporter molecule and a quencher molecule and is cleaved by 5' nuclease.

FIG. 8 shows the results of the detection of *Neisseria gonorrhoeae* gene by PCE-SC assay using both an upstream primer to the PO and an upstream oligonucleotide to the SO. The SO has a reporter molecule and a quencher molecule.

FIG. 9 shows the results of the detection of *Neisseria gonorrhoeae* gene by PCE-SC assay with no use of an upstream primer to the PTO. The upstream oligonucleotide to the SO is used. The SO has a reporter molecule and a quencher molecule.

FIG. 10 shows the results of the detection of *Neisseria gonorrhoeae* gene by PCE-SC assay using a pair of upstream and downstream primers to the PTO. The upstream oligonucleotide to the SO is used. The SO has a reporter molecule and a quencher molecule.

DETAILED DESCRIPTION OF THIS INVENTION

Figure 1:
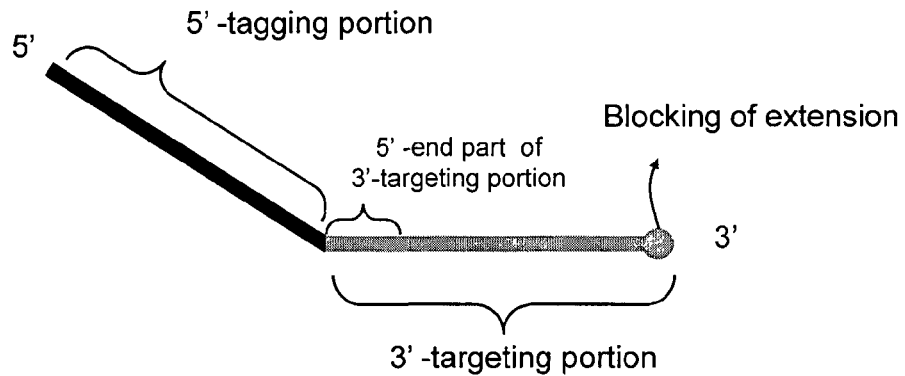
FIG. 1A shows the schematic structures of PTO (Probing and Tagging Oligonucleotide)
FIG. 1B shows CTO (Capturing and Templating Oligonucleotide) and FIG. 1C shows SO (Signaling Oligonucleotide) each as used in PTO Cleavage and Extension-Dependent Signaling Oligonucleotide Cleavage assay (PCE-SC assay). The 3'-ends of the PTO, CTO and SO may be blocked to prohibit their extension.
Figure 1:
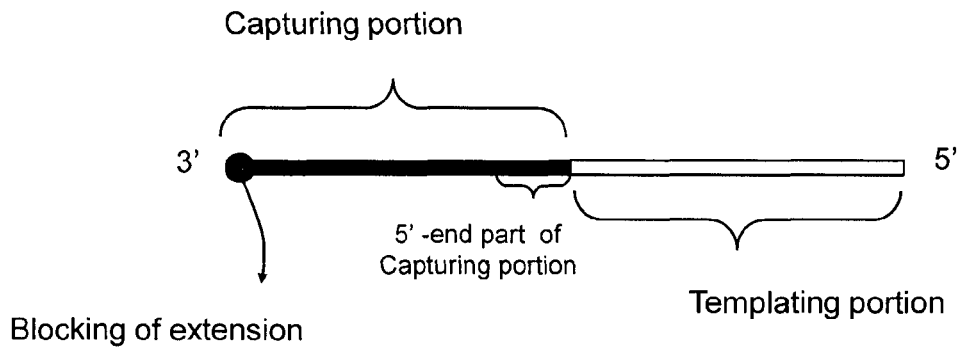
Figure 1:
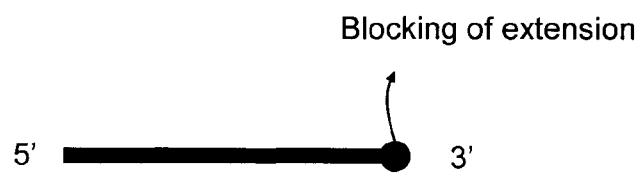

The present invention is generally drawn to a novel method for detecting a target nucleic acid sequence by a PCE-SC (PTO Cleavage and Extension-Dependent Signaling Oligonucleotide Cleavage) assay.

The PCE-SC assay of the present invention will be described in more detail as follows:

I. Target Nucleic Acid Detection by a PCE-SC Assay

In one aspect of the present invention, there is provided a method for detecting a target nucleic acid sequence from a DNA or a mixture of nucleic acids by a PCE-SC (PTO Cleavage and Extension-Dependent Signaling Oligonucleotide Cleavage) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5'-nuclease activity under conditions for cleavage of the PTO; wherein the upstream oligonucleotide or its extended strand induces cleavage of the PTO by the enzyme having a 5'-nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a template portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase, wherein the fragment hybridized with the capturing portion of the CTO is extended to form an extended strand comprising an extended sequence complementary to the templating portion of the CTO, thereby forming an extended duplex;

(e) hybridizing the extended strand with SO (Signaling Oligonucleotide) to form an extended strand/SO hybrid; wherein the SO comprises a hybridizing nucleotide sequence complementary to the extended strand and at least one label;

(f) cleaving the SO of the extended strand/SO hybrid using a nucleolytic enzyme to generate a cleaved fragment of the SO; and (g) detecting the occurrence of the cleavage reaction in the step (f); wherein the detection is performed by measuring a signal provided from the label linked to the SO, whereby the occurrence of the cleavage reaction of the SO of the extended strand/SO hybrid indicates the presence of the target nucleic acid sequence.

The present inventors have made intensive researches to develop novel approaches to detect target sequences with more improved accuracy and convenience, inter alia, in a multiplex manner. As a result, we have established novel protocols for detection of target sequences, in which target detection is accomplished using enzymatic reactions such as 5' nucleolytic reaction and extension, and extension-dependent hybridization and cleavage reactions as well as probe hybridization, contributing to improvements in the target specificity, process convenience and workability in multiplex detection.

The present invention employs successive events followed by probe hybridization, including the cleavage and extension of a PTO (Probing and Tagging Oligonucleotide), and the extension-dependent signaling oligonucleotide cleavage reaction; therefore, it is named as a PCE-SC (PTO Cleavage and Extension-Dependent Signaling Oligonucleotide Cleavage) assay.

The PCE-SC assay of the present invention will be described with reference to each step as follows:

Step (a): Hybridization of an Upstream Oligonucleotide and a PTO with a Target Nucleic Acid Sequence According to the present invention, a target nucleic acid sequence is first hybridized with an upstream oligonucleotide and a PTO (Probing and Tagging Oligonucleotide).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

In a certain embodiment, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with the upstream oligonucleotide and the PTO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO) and the target nucleotide sequence. For instance, when a relatively short oligonucleotide is used, it is suitable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", for instance, perfectly complementary.

The 5'-tagging portion of the PTO comprises a nucleotide sequence non-complementary to the target nucleic acid sequence. The templating portion of the CTO (Capturing and Templating Oligonucleotide) comprises a nucleotide sequence non-complementary to the 5'-tagging portion and the 3'-targeting portion of the PTO. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", for instance, perfectly non-complementary.

For example, the term "non-complementary" in conjunction with the 5'-tagging portion of the PTO means that the 5'-tagging portion is sufficiently non-complementary not to hybridize selectively to a target nucleic acid sequence under the designated annealing conditions or stringent conditions, encompassing the terms "substantially non-complementary" and "perfectly non-complementary", for instance, perfectly non-complementary.

The term used herein "PTO (Probing and Tagging Oligonucleotide)" means an oligonucleotide comprising (i) a 3'-targeting portion serving as a probe and (ii) a 5'-tagging portion with a nucleotide sequence non-complementary to the target nucleic acid sequence, which is nucleolytically released from the PTO after hybridization with the target nucleic acid sequence. The 5'-tagging portion and the 3'-targeting portion in the PTO have to be positioned in a 5' to 3' order. The PTO is schematically illustrated in FIG. 1.

In an embodiment, the hybridization in step (a) is preformed under stringent conditions that the 3'-targeting portion is hybridized with the target nucleic acid sequence and the 5'-tagging portion is not hybridized with the target nucleic acid sequence.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the templating portion of the CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. In certain embodiment, the 3'-end of the PTO is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO may be designed to have a hairpin structure.

The non-hybridization between the 5'-tagging portion of the PTO and the target nucleic acid sequence refers to non-formation of a stable double-strand between them under certain hybridization conditions. According to an embodiment of this invention, the 5'-tagging portion of the PTO not involved in the hybridization with the target nucleic acid sequence forms a single-strand.

The upstream oligonucleotide is located upstream of the PTO.

In addition, the upstream oligonucleotide or its extended strand hybridized with the target nucleic acid sequence induces cleavage of the PTO by an enzyme having a 5' nuclease activity.

The induction of the PTO cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO sufficient to induce the PTO cleavage by an enzyme having a 5' nuclease activity, the enzyme bound to the upstream oligonucleotide digests the PTO with no extension reaction. In contrast, where the upstream oligonucleotide is positioned distantly to the PTO, an enzyme having a polymerase activity (e.g., template-dependent polymerase) catalyzes extension of the upstream oligonucleotide (e.g., upstream primer) and an enzyme having a 5' nuclease activity bound to the extended product digests the PTO.

Therefore, the upstream oligonucleotide may be located relatively to the PTO in two fashions. The upstream oligonucleotide may be located adjacently to the PTO sufficient to induce the PTO cleavage in an extension-independent manner. Alternatively, the upstream oligonucleotide may be located distantly to the PTO sufficient to induce the PTO cleavage in an extension-dependent manner.

The term used herein "adjacent" with referring to positions or locations means that the upstream oligonucleotide is located adjacently to the 3'-targeting portion of the PTO to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to an embodiment, the upstream oligonucleotide is located distantly to the PTO sufficient to induce the PTO cleavage in an extension-dependent manner.

According to an embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-part of the 3'-targeting portion of the PTO. In certain embodiment, the overlapped sequence is 1-10 nucleotides, 1-5 nucleotides or 1-3 nucleotides in length. Where the upstream oligonucleotide has a partial-overlapped sequence with the 5'-part of the 3'-targeting portion of the PTO, the 3'-targeting portion is partially digested along with the 5'-tagging portion in the cleavage reaction of the step (b). In addition, the overlapped sequence permits to cleave a desired site of the 3'-targeting portion.

According to an embodiment, the upstream primer induces through its extended strand the cleavage of the PTO by the enzyme having the 5' nuclease activity.

The conventional technologies for cleavage reactions by upstream oligonucleotides may be applied to the present invention, so long as the upstream oligonucleotide induces cleavage of the PTO hybridized with the target nucleic acid sequence to release a fragment comprising the 5'-tagging portion or a part of the 5'-tagging portion of the PTO. For example, U.S. Pat. Nos. 5,210,015, 5,487,972, 5,691,142, 5,994,069 and 7,381,532 and U.S. Appln. Pub. No. 2008-0241838 may be applied to the present invention.

According to an embodiment, the method is performed in the presence of a downstream primer. The downstream primer generates additionally a target nucleic acid sequence to be hybridized with the PTO, enhancing sensitivity in a target detection.

According to an embodiment, when the upstream primer and the downstream primer are used, a template-dependent nucleic acid polymerase is additionally employed for extension of the primers.

According to an embodiment, the upstream oligonucleotide (upstream primer or upstream probe), the downstream primer and/or 5'-tagging portion of the PTO have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35:6e40(2007)).

According to an embodiment, the 3'-targeting portion of the PTO has a modified dual specificity oligonucleotide (mDSO) structure developed by the present inventor. The modified dual specificity oligonucleotide (mDSO) structure shows significantly improved target specificity compared with conventional probes (see WO 2011/028041).

Step (b): Release of a Fragment from the PTO Cleavage

Afterwards, the resultant of the step (a) is contacted to an enzyme having a 5' nuclease activity under conditions for cleavage of the PTO. The PTO hybridized with the target nucleic acid sequence is digested by the enzyme having the 5' nuclease activity to release a fragment comprising the 5'-tagging portion or a part of the 5'-tagging portion of the PTO.

The term used herein "conditions for cleavage of the PTO" means conditions sufficient to digest the PTO hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, $MgCl_2$ and temperature.

Figure 2:
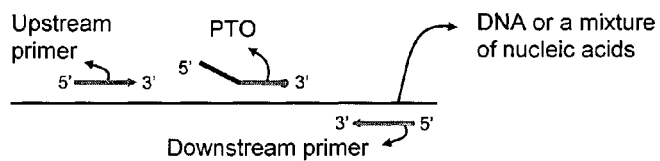
FIGS. 2A, 2B, 2C, 2D and 2E schematically represent one embodiment of PCE-SC assay.
Figure 2:
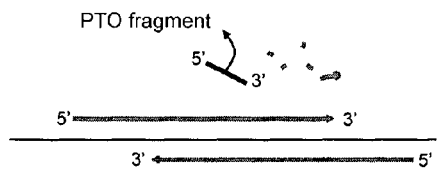
Figure 2:
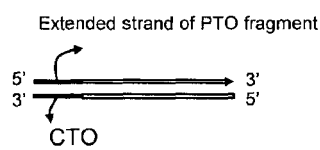
Figure 2:
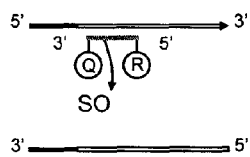
Figure 2:
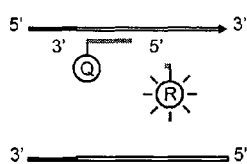

When the PTO is hybridized with the target nucleic acid sequence, its 3'-targeting portion is involved in the hybridization and the 5'-tagging portion forms a single-strand with no hybridization with the target nucleic acid sequence (see FIG. 2). As such, an oligonucleotide comprising both single-stranded and double-stranded structures may be digested using an enzyme having a 5' nuclease activity by a variety of technologies known to one of skill in the art.

The cleavage sites of the PTO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO, releasing a fragment comprising the 5'-tagging portion or a part of the 5'-tagging portion.

Briefly, there may be three sites of cleavage in the step (b). Firstly, the cleavage site is a junction site between a hybridization portion of the PTO (3'-targeting portion) and a non-hybridization portion (5'-tagging portion). The second cleavage site is a site located several nucleotides in a 3'-direction apart from the 3'-end of the 5'-tagging portion of the PTO. The second cleavage site is located at the 5'-end part of the 3'-targeting portion of the PTO. The third cleavage site is a site located several nucleotides in a 5'-direction apart from the 3'-end of the 5'-tagging portion of the PTO.

According to an embodiment, the initial site for the cleavage of the PTO by the template-dependent polymerase having the 5' nuclease activity upon extension of the upstream primer is a starting point of the double strand between the PTO and the target nucleic acid sequence or a site 1-3 nucleotides apart from the starting point.

In this regard, the term used herein "a fragment comprising the 5'-tagging portion or a part of the 5'-tagging portion of the PTO" in conjunction with cleavage of the PTO by the enzyme having the 5' nuclease activity is used to encompass (i) the 5'-tagging portion, (ii) the 5'-tagging portion and the 5'-end part of the 3'-targeting portion and (iii) a part of the 5'-tagging portion. In this application, the term "a fragment comprising the 5'-tagging portion or a part of the 5'-tagging portion of the PTO" may be also described as "PTO fragment".

According to an embodiment, the PTO has a blocker portion containing a blocker resistant to cleavage by the enzyme having 5' nuclease activity and the blocker portion is used to control an initial cleavage site and/or successive cleavages.

According to an embodiment, the PTO has a blocker portion containing as a blocker at least one nucleotide resistant to cleavage by the enzyme having 5' nuclease activity.

For example, to induce cleavage at the junction site between a hybridization portion of the PTO (3'-targeting portion) and a non-hybridization portion (5'-tagging portion), the 5'-end part of 3'-targeting portion of PTO may be blocked with blockers.

The number of blockers contained in the blocker portion may be not limited, including 1-10, 2-10, 3-8 or 3-6 blockers. The blockers present in the PTO may be in a continuous or intermittent manner, suitably a continuous manner. The nucleotides as blockers with a backbone resistant to the 5' to 3' exonuclease activity include any one known to one of skill in the art. For example, it includes various phosphorothioate linkages, phosphonate linkages, phosphoroamidate linkages and 2'-carbohydrates modifications. According to an embodiment, nucleotides having a backbone resistant to the 5' to 3' exonuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

According to an embodiment, a nucleotide as a blocker includes LNA(locked nucleic acid).

The term "part" used in conjunction with the PTO or CTO such as the part of the 5'-tagging portion of the PTO, the 5'-end part of the 3'-targeting portion of the PTO and the 5'-end part of the capturing portion of the CTO refers to a nucleotide sequence composed of 1-40, 1-30, 1-20, 1-15, 1-10 or 1-5 nucleotides, suitably 1, 2, 3 or 4 nucleotides.

According to an embodiment, the enzyme having the 5' nuclease activity is DNA polymerase having a 5' nuclease activity or FEN nuclease, suitably a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis, Thermis flavus, Thermococcus literalis, Thermus antranikanii, Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosiphoafricanus, Pyrococcus woesei, Pyrococcus horikoshii, Pyrococcus abyssi, Pyrodictium occultum, Aquifex pyrophilus* and *Aquifex aeolieus*. In certain embodiment, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataficus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii, Aeropyrum pernix,* and *Archaeaglobus veneficus*.

Where the upstream primer is used in the step (a), the conditions for cleavage of the PTO may comprise extension reaction of the upstream primer.

According to an embodiment, the upstream primer is used in the step (a), a template-dependent polymerase is used for extension of the upstream primer and the template-dependent polymerase is identical to the enzyme having the 5' nuclease activity.

Optionally, the upstream primer is used in the step (a), a template-dependent polymerase is used for extension of the upstream primer and the template-dependent polymerase is different from the enzyme having the 5' nuclease activity.

Step (c): Hybridization of the Fragment Released from the PTO with CTO

The fragment released from the PTO is hybridized with a CTO (Capturing and Templating Oligonucleotide).

The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The CTO acts as a template for extension of the fragment released from the PTO. The fragment serving as a primer is hybridized with the CTO and extended to form an extended duplex.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

As described above, when the fragment having the 5'-tagging portion of the PTO is released, the capturing portion of the CTO may be designed to comprise a nucleotide sequence complementary to the 5'-tagging portion. When the fragment having the 5'-tagging portion and a 5'-end part of the 3'-targeting portion is released, the capturing portion of the CTO may be designed to comprise a nucleotide sequence complementary to the 5'-tagging portion and the 5'-end part of the 3'-targeting portion. When the fragment having a part of the 5'-tagging portion of the PTO is released, the capturing portion of the CTO may be designed to comprise a nucleotide sequence complementary to the part of the 5'-tagging portion.

Moreover, it is possible to design the capturing portion of the CTO with anticipating cleavage sites of the PTO. For example, where the capturing portion of the CTO is designed to comprise a nucleotide sequence complementary to the 5'-tagging portion, either the fragment having a part of the 5'-tagging portion or the fragment having the 5'-tagging portion can be hybridized with the capturing portion and then extended. Where the fragment comprising the 5'-tagging portion and a 5'-end part of the 3'-targeting portion is released, it may be hybridized with the capturing portion of the CTO designed to comprise a nucleotide sequence complementary to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-3 mismatch nucleotides).

When the fragment comprising the 5'-tagging portion and a 5'-end part of the 3'-targeting portion is released, the 5'-end part of the capturing portion of the CTO may be designed to have a nucleotide sequence complementary to the cleaved 5'-end part of the 3'-targeting portion, overcoming problems associated with mismatch nucleotides.

In an embodiment, the nucleotide sequence of the 5'-end part of the capturing portion of the CTO complementary to the cleaved 5'-end part of the 3'-targeting portion may be selected depending on anticipated cleavage sites on the 3'-targeting portion of the PTO. The nucleotide sequence of the 5'-end part of the capturing portion of the CTO complementary to the cleaved 5'-end part of the 3'-targeting portion may be 1-10 nucleotides, 1-5 nucleotides or 1-3 nucleotides in length.

The 3'-end of the CTO may comprise additional nucleotides not involved in hybridization with the fragment. Moreover, the capturing portion of the CTO may comprise a nucleotide sequence complementary only to a part of the fragment (e.g., a part of the fragment containing its 3'-end portion) so long as it is stably hybridized with the fragment.

The term used "capturing portion comprising a nucleotide sequence complementary to the 5'-tagging portion or a part of the 5'-tagging portion" is described herein to encompass various designs and compositions of the capturing portion of the CTO as discussed above.

The CTO may be designed to have a hairpin structure.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. In certain embodiment, the 3'-end of the CTO is blocked to prohibit its extension. The non-extendible blocking of the CTO may be achieved in accordance with conventional methods. For instance, the blocking may be performed by adding to the 3'-hydroxyl group of the last nucleotide of the CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The fragment released from the PTO is hybridized with the CTO, providing a form suitable in extension of the fragment. Although an undigested PTO is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

Step (d): Extension of the Fragment

The extension reaction is carried out using the resultant of the step (c) and a template-dependent nucleic acid polymerase. The fragment hybridized with the capturing portion of the CTO is extended to form an extended strand comprising an extended sequence complementary to the templating portion of the CTO, thereby forming an extended duplex. In contrast, uncleaved PTO hybridized with the capturing portion of the CTO is not extended such that no extended duplex is formed.

The term used herein "extended duplex" means a duplex formed by extension reaction in which the fragment hybridized with the capturing portion of the CTO is extended using the templating portion of the CTO as a template and the template-dependent nucleic acid polymerase.

The term used herein "extended strand" in conjunction with the fragment means a sequence composed of the fragment and its extended sequence.

The term used herein "extended sequence" in conjunction with the fragment means only a newly extended sequence which is a portion of the extended strand except the fragment.

The template-dependent nucleic acid polymerase used in the step (d) may include any nucleic acid polymerases, for example, Klenow fragment of *E. coli* DNA polymerase I, a thermostable DNA polymerase and bacteriophage T7 DNA polymerase. Preferably, the polymerase is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis, Thermus antranikianii, Thermus caldophilus, Thermus chliarophilus, Thermus flavus, Thermus igniterrae, Thermus lacteus, Thermus oshimai, Thermus rube Thermus rubens, Thermus scotoductus, Thermus silvans, Thermus* species Z05, *Thermus* species sps 17, *Thermus thermophilus, Thermotoga maritima, Thermotoga neapolitana, Thermosipho africanus, Thermococcus litoralis; Thermococcus barossi, Thermococcus gorgonarius, Thermotoga maritima, Thermotoga neapolitana, Thermosiphoafricanus, Pyrococcus furiosus*(Pfu), *Pyrococcus woesei, Pyrococcus horikoshii, Pyrococcus abyssi, Pyrodictium occultum, Aquifex pyrophilus* and *Aquifex aeolieus*. Particularly, the template-dependent nucleic acid polymerase is Taq polymerase.

According to an embodiment, the enzyme having the 5' nuclease activity used in the step (b) is identical to the template-dependent nucleic acid polymerase used in the step (d). More particularly, the enzyme having the 5' nuclease activity used in the step (b), the template-dependent nucleic acid polymerase used for extension of the upstream primer and the template-dependent nucleic acid polymerase used in the step (d) are identical to one another.

Step (e): Hybridization of Extended Strand with SO

Following the extension reaction, the extended strand is hybridized with SO (Signaling Oligonucleotide) to form an extended strand/SO hybrid.

The SO to be hybridized with the extended strand comprises a hybridizing nucleotide sequence complementary to the extended strand, and at least one label.

The term used herein "hybridizing nucleotide sequence complementary to the extended strand" in conjunction with the SO refers to a sequence capable of forming a double strand with the extended strand under certain stringent conditions, resulting in formation of a hybrid with the extended strand.

According to an embodiment, the SO may comprise, throughout its whole sequence or partial sequence, a hybridizable sequence to the extended sequence.

The term used herein "hybridizable sequence to the extended sequence" in conjunction with the SO refers to certain sequence involving in forming a double strand with the extended sequence among the sequence of SO.

For instance, the SO may comprise, throughout its whole sequence, a hybridizable sequence to the extended sequence. Alternatively, one portion of the SO may comprise a complementary sequence to the extended sequence (i.e. the portion is a hybridizable sequence to the extended sequence) and the other portion may comprise a complementary sequence to the PTO fragment, so long as the SO may form a double strand with the extended strand in the step (e).

Particularly, the SO may comprise, throughout its whole sequence, a hybridizable sequence to the extended sequence.

Where the SO comprising a complementary sequence only to the PTO fragment in the extended strand is used and a cleavage site for a nucleolytic enzyme is provided by its hybridization, a hybrid between 5'-tagging portion of an uncleaved PTO and SO is likely to be cleaved to generate a non-target signal. However, where the SO is designed to comprise a hybridizable sequence to the extended sequence newly synthesized in the extension reaction, non-target signals may be excluded. For example, a cleavage site for a nucleolytic enzyme may be designed to be provided only when at least a portion of the SO is hybridized to the extended sequence newly synthesized in the SO/extended strand hybrid. In the above case, a cleavage site for a nucleolytic enzyme may not be provided when the SO is hybridized with an uncleaved PTO.

In certain embodiment, the sequence of the SO is selected not to form a hybrid with an undigested PTO. For example, the complementarity between the SO and the 5'-tagging portion of an undigested PTO may be less than 90%, 70%, 50%, 30% or 20%, which may be varied depending on hybridization conditions for formation of the extended strand/SO hybrid.

The SO may have any length, for example, 5-100 nucleotides, 5-80 nucleotides, 5-60 nucleotides, 5-40 nucleotides, 5-20 nucleotides, 5-10 nucleotides, 10-100 nucleotides, 10-80 nucleotides, 10-60 nucleotides, 10-40 nucleotides, 10-30 nucleotides, 10-20 nucleotides, 15-100 nucleotides, 15-80 nucleotides, 15-60 nucleotides, 15-40 nucleotides, 15-30 nucleotides, 15-20 nucleotides, 20-100 nucleotides, 20-80 nucleotides, 20-60 nucleotides, 20-40 nucleotides or 20-30 nucleotides.

The SO may have a hairpin structure. In certain embodiment, the 3'-end of the SO is blocked to prohibit its extension. Alternatively, the SO having a non-blocked 3'-OH end may be extended.

In an embodiment of this invention, the SO is a 5'-tagged SO comprising at its 5'-direction a 5'-tagging portion having a non-complementary sequence to the extended strand. The portion (5'-tagging portion) having a non-complementary sequence to the extended strand may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

In certain embodiment, the hybridization of the step (e) is carried out in the presence of an upstream oligonucleotide located upstream of the SO. The upstream oligonucleotide comprises a complementary sequence to the extended strand and is hybridized upstream of the SO with the extended strand. In another embodiment, the upstream oligonucleotide is an upstream primer or an upstream probe.

The hybridization between the extended strand and the SO results in generation of the cleavage site for a nucleolytic enzyme such as a 5' nuclease, a ribonuclease or a restriction enzyme. The cleavage site on the SO is a site generated only when the extended strand/SO hybrid is formed.

In an embodiment, the formation of the extended strand/SO hybrid in the step (e) produces a cleavage site for a 5' nuclease. The cleavage site on the SO is a site generated only when the extended strand/SO hybrid is formed, and the SO of the extended strand/SO hybrid is cleaved in a 5' to 3' direction by the 5' nuclease.

In an embodiment, the SO comprises a RNA sequence and the formation of the extended strand/SO hybrid in the step (e) produces a DNA-RNA hybrid duplex and a cleavage site for a ribonuclease.

In an embodiment, the SO comprises a sequence recognized by the restriction enzyme and the formation of the extended strand/SO hybrid in the step (e) produces a cleavage site for the restriction enzyme.

In certain embodiment, the formation of the extended strand/SO hybrid in the step (e) produces a cleavage site for a nucleolytic enzyme capable of cleaving a DNA duplex, a RNA duplex or a DNA-RNA hybrid duplex.

The extended strand of the PTO fragment and/or the SO may be designed such that a desired type of cleavage sites for nucleolytic enzymes is introduced.

Where cleavage sites for nucleolytic enzymes acting on a DNA duplex (e.g., 5' nucleases and restriction enzymes) is intended to generate, the extended strand of the PTO fragment and the SO each composed of DNA molecules are particularly used. The extended strand of the PTO fragment composed of DNA molecules is hybridized with the SO composed of DNA molecules to generate a cleavage site for nucleolytic enzymes acting on a DNA duplex (e.g., 5' nucleases and restriction enzymes).

Where the present invention uses a restriction enzyme, the extended strand of the PTO fragment and the SO comprises particularly a sequence recognized by the restriction enzyme. The extended strand/SO hybrid having the cleavage sit for the restriction enzyme is cleaved by the restriction enzyme to produce a cleaved fragment, indicating the presence of target nucleic acid sequences.

Where cleavage sites for nucleolytic enzymes acting on a DNA-RNA hybrid duplex (e.g., RNase H) are intended to generate, the extended strand of the PTO fragment composed of DNA molecules and the SO composed of RNA molecules are particularly used. In an embodiment, the SO comprises 1-10 ribonucleotides.

The extended strand of the PTO fragment composed of DNA molecules is hybridized with the SO composed of RNA molecules to generate a cleavage site for nucleolytic enzymes acting on a DNA-RNA hybrid duplex (e.g., RNase H).

In an embodiment, the present method further comprises a denaturation step between the steps (d) and (e).

The formation of the extended duplex between the extended strand and the CTO may be responsible for low hybridization efficiency between the SO and the extended strand. In the present invention, the increase in the amount of the extended strand is likely to increase probability of occurrence of not only hybridization between the extended strand and the SO but also successive cleavage reaction.

According to an embodiment, the amount of the PTO is larger than that of the CTO (e.g., the mole ratio of the PTO to the CTO of more than 1.0) and the steps (a)-(f) are repeated with denaturation between repeating cycles. In such case, the number of the extended strand becomes increased, while the number of the CTO is constant. Therefore, free extended strands not hybridized with the CTO may exist even under conditions allowing the formation of the extended duplex between the extended strand and the CTO. The SO may be effectively hybridized with the free extended strands with no interference by the CTO.

The SO is labeled with at least one label capable of providing signal indicating the occurrence of the cleavage reaction of the extended strand/SO hybrid (i.e., the presence of target nucleic acid sequences).

Step (f): Cleavage of Extended Strand/SO Hybrid

The SO of the extended strand/SO hybrid is cleaved using a nucleolytic enzyme to generate a cleaved fragment of the SO. In the present specification, the cleavage reaction in the step (b) is referred to as a first cleavage reaction and that in the step (f) as a second cleavage reaction.

The second cleavage reaction becomes realized because an action site for a nucleolytic enzyme is generated in the extended strand/SO hybrid formed by the hybridization in the step (e).

In an embodiment of this invention, the cleaved fragment of the SO of the extended strand/SO hybrid may be in a single strand or double strand and the cleavage may form at least two fragments. For example, the cleavage of the SO of the extended strand/SO hybrid by restriction enzymes forms two cleaved fragments in a double stand and the double-stranded fragments may be dissociated to a single stand form depending on reaction conditions. In the cleavage reaction using 5' nucleases, a single-strand fragment may be formed.

Nucleolytic enzymes used in the second cleavage reaction include any enzymes known to one of skill in the art.

In certain embodiment, the nucleolytic enzyme used in the second cleavage reaction includes a 5' nuclease, a restriction enzyme and a ribonuclease, particularly a thermostable 5' nuclease, restriction enzyme and ribonuclease.

In another embodiment, the nucleolytic enzyme used in the second cleavage reaction includes a nucleolytic enzyme acting specifically on a duplex molecule.

In certain embodiment, the nucleolytic enzyme is a 5' nuclease and the formation of the extended strand/SO hybrid in the step (e) produces a cleavage site for the 5' nuclease, whereby the SO of the extended strand/SO hybrid is cleaved in a 5' to 3' direction by the 5' nuclease. Particularly, the 5' nuclease is a template-dependent DNA polymerase or FEN nuclease having a 5' nuclease activity.

Figure 5:
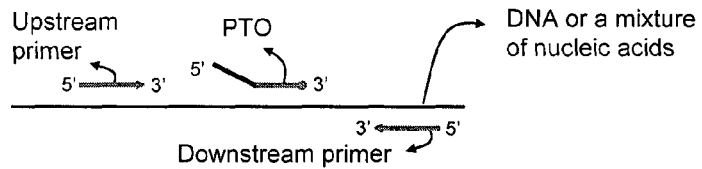
FIGS. 5A, 5B, 5C, 5D and 5E schematically represent still yet another embodiment of PCE-SC assay using an upstream primer as upstream oligonucleotides to the SO.
Figure 5:
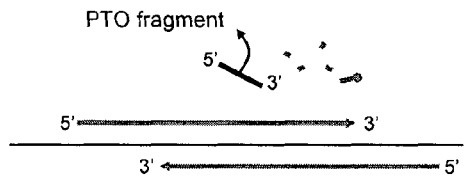
Figure 5:
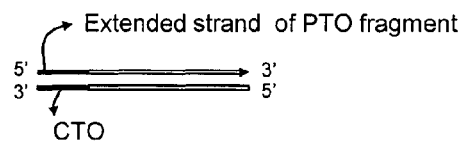
Figure 5:
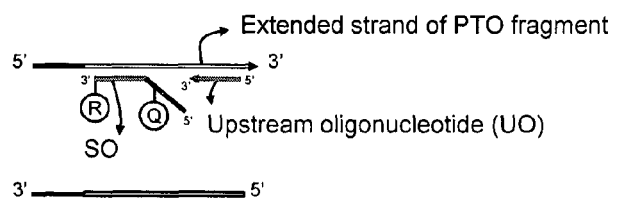
Figure 5:
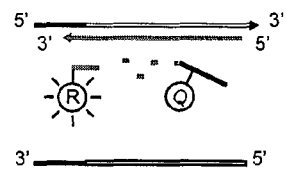

Of nucleolytic enzymes, the 5' nuclease cleaves a DNA duplex in a 5' to 3' direction. In certain embodiment, the 5' nuclease is one having a 5' to 3' exonuclease activity, 5' to 3' endonuclease or both of them. As represented in FIGS. 2 and 5, the PTO fragment formed by cleavage of the PTO hybridized with the target nucleic acid sequence is hybridized with the CTO and then extended to form the extended strand, after which the SO is hybridized with the extended strand to form the extended strand/SO hybrid. The 5'-end portion of the SO of the extended strand/SO hybrid is cleaved by the 5' nuclease to generate a cleaved fragment indicating the presence of target nucleic acid sequences.

Template-dependent DNA polymerases having a 5' nuclease activity have a 5' to 3' exonuclease activity and in some polymerases, even a 5' to 3' endonuclease activity.

Template-dependent DNA polymerases having a 5' nuclease activity may induce upstream oligonucleotide-dependent cleavage reaction as the step (b) (see, U.S. Pat. No. 5,210,015). In addition, they may also induce upstream oligonucleotide-independent cleavage reaction (see, lawyer et al, *Genome Res.* 1993, 2:275-287 and WO 2008/011004).

In an embodiment of this invention, the 5' nuclease is a template-dependent DNA polymerase having a 5' nuclease activity, particularly a thermostable DNA polymerase. The thermostable DNA polymerase can be described in detail with referring to descriptions in the step (b). Preferably, the 5' nuclease for cleavage of the SO of the extended strand/SO hybrid is Taq polymerase.

According to an embodiment of this invention, both the enzyme having a 5'-nuclease activity in the step (b) and the nucleolytic enzyme in the step (f) are a template-dependent DNA polymerase having a 5' nuclease activity.

In certain embodiment, the template-dependent DNA polymerase having a 5' nuclease activity may induce upstream oligonucleotide-independent cleavage reaction to digest the extended strand/SO hybrid in the step (e) as well as upstream oligonucleotide-independent cleavage reaction in the step (b).

According to an embodiment, the cleavage of the extended strand/SO hybrid by the template-dependent DNA polymerase having an upstream oligonucleotide-independent 5' nuclease activity may be affected by positions of labels or linkage types of labels present in the extended strand/SO hybrid. Particularly, where a label is linked to the 5'-end of the SO of the extended strand/SO hybrid, the cleavage of the extended strand/SO hybrid by the template-dependent DNA polymerase having a 5' nuclease activity may be more efficient if the label is linked to a phosphate group of the 5'-end of the SO, particularly through a carbon-spacer. Where the label is linked to a base of the 5'-end of the SO or the carbon-spacer is not used, the cleavage of the extended strand/SO hybrid is unlikely to occur.

Among nucleolytic enzymes, the restriction enzyme cleaves a cleavage site for restriction enzymes generated by the formation of the extended strand/SO hybrid in the step (e). The PTO fragment formed by cleavage of the PTO hybridized with the target nucleic acid sequence is hybridized with the CTO (comprising a sequence recognized by the restriction enzyme) and then extended to introduce a recognition sequence of the restriction enzyme into the extended sequence of the PTO fragment, after which the SO comprising a sequence recognized by the restriction enzyme is hybridized with the extended strand of the PTO fragment to produce a cleavage site for the restriction enzyme. The restriction enzyme endonucleolytically cleaves the extended strand/SO hybrid to form the cleaved fragment indicating the presence of the target nucleic acid sequence.

According to an embodiment, the restriction enzyme is a restriction enzyme specifically recognizing and digesting a specific sequence of a duplex, particularly a thermostable restriction enzyme. Various restriction enzymes known in the art may be used.

According to an embodiment, the nucleolytic enzyme is a ribonuclease, the SO comprises a RNA sequence and the formation of the extended strand/SO hybrid in the step (e) produces a DNA-RNA hybrid duplex to form a cleavage site for the ribonuclease. The cleavage site for the ribonuclease is cleaved by the ribonuclease in the step (f) to form the cleaved fragment indicative of the presence of the target nucleic acid sequence.

According to an embodiment, the ribonuclease used in the present invention is RNase H or Exo III.

RNase H is one of endoribonucleases capable of digesting a RNA portion of a DNA-RNA hybrid duplex. Where RNase H is used, the SO may comprise a RNA molecule. The PTO fragment formed by cleavage of the PTO hybridized with the target nucleic acid sequence is hybridized with the capturing portion of the CTO and then extended, and the SO is hybridized with the extended strand of the PTO fragment. The RNA molecule in the SO of the extended strand/SO hybrid is endonucleolytically cleaved to form the cleaved fragment indicating the presence of the target nucleic acid sequence.

Exo III has been reported to have RNase activities (Mol C D, et al., *Nature* 374(6520):381386(1995)). Where Exo III is used, the cleaved fragment indicating the presence of the target nucleic acid sequence is formed in the same fashion as RNase H.

Where the SO comprising a RNA molecule, it comprises wholly or partially the RNA molecule.

The step (f) may be performed in the presence or absence of an upstream oligonucleotide to the SO. In such case, the upstream oligonucleotide to the SO is an upstream primer or an upstream probe.

In certain embodiment, the step (f) is carried out in the presence of an upstream oligonucleotide to the SO.

In an embodiment of this invention, the nucleolytic enzyme is a 5' nuclease and the step (f) is performed in the presence of an upstream oligonucleotide located upstream of the SO, such that the SO of the extended strand/SO hybrid is cleaved by the nucleolytic activity of the 5' nuclease dependent on the upstream oligonucleotide or its extended strand.

In certain embodiment, the nucleolytic enzyme is a thermostable nucleolytic enzyme.

Figure 3:
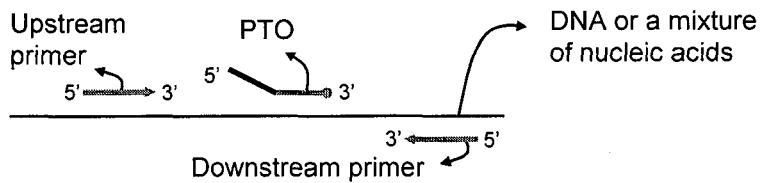
FIGS. 3A, 3B, 3C, 3D and 3E schematically represent another embodiment of PCE-SC assay using an upstream probe as upstream oligonucleotides to the SO.
Figure 3:
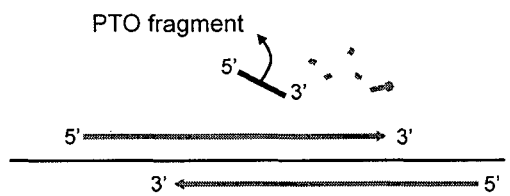
Figure 3:
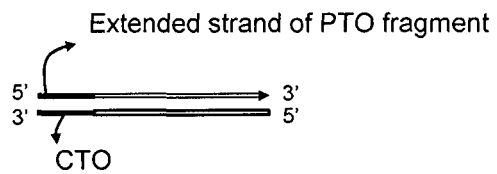
Figure 3:
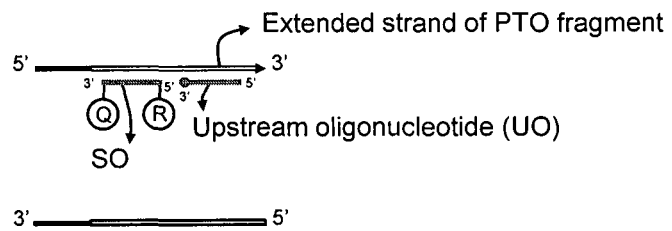
Figure 3:
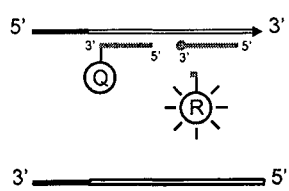
Figure 4:
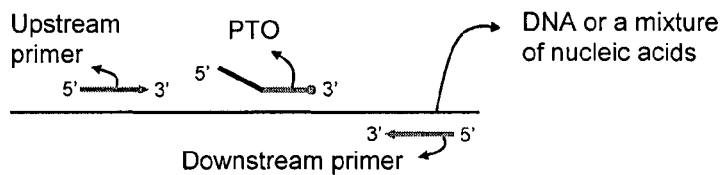
FIGS. 4A, 4B, 4C, 4D and 4E schematically represent still another embodiment of PCE-SC assay using an upstream primer as upstream oligonucleotides to the SO.
Figure 4:
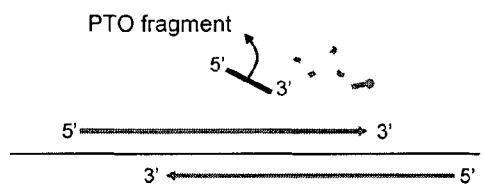
Figure 4:
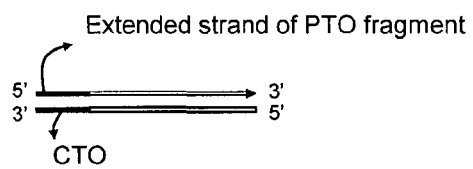
Figure 4:
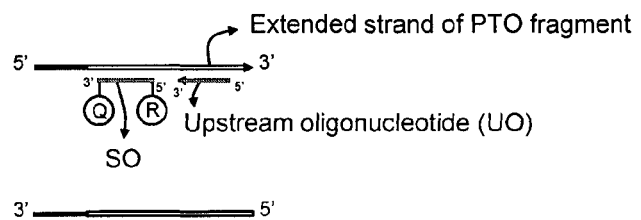
Figure 4:
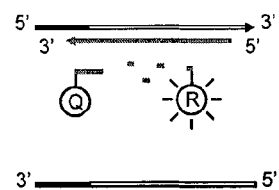
Figure 6:
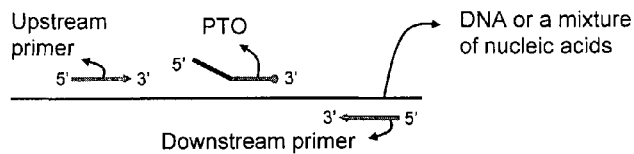
FIGS. 6A, 6B, 6C, 6D and 6E schematically represent further embodiment of PCE-SC assay on a solid phase.
Figure 6:
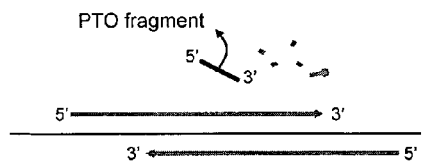
Figure 6:
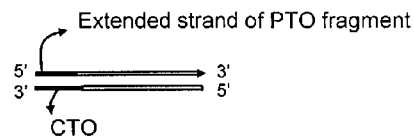
Figure 6:
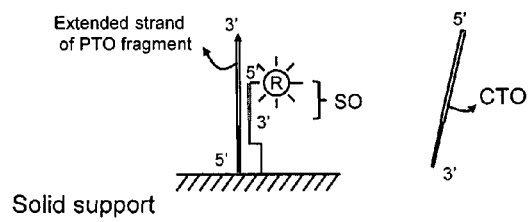
Figure 6:
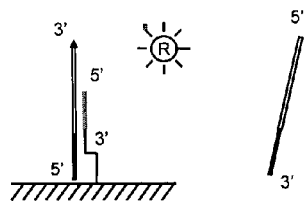

FIGS. 2 and 6 illustrate specific embodiments of this invention carried in the absence of the upstream oligonucleotide to the SO, and FIGS. 3-5 represent specific embodiments carried in the presence of the upstream oligonucleotide to the SO.

According to an embodiment, the upstream oligonucleotide-independent cleavage of the extended strand/SO hybrid by the 5' nuclease activity of the template-dependent DNA polymerase may have low cleavage efficiency than the upstream oligonucleotide-dependent cleavage by the 5' nuclease activity of the template-dependent DNA polymerase.

The details of the upstream oligonucleotide to the SO may be described with reference to those of the upstream oligonucleotide to the PTO in the step (a).

In an embodiment, an upstream oligonucleotide (particularly, upstream primer) to the SO can be employed when a ribonuclease or a restriction enzyme is used for nucleolytic enzyme. In such case, DNA polymerase having no 5' nuclease activity may be used only for extension of the upstream primer.

In an embodiment of the present invention, the SO comprises a 5'-tagging portion comprising in its 5'-direction a non-complementary sequence to the extended strand. In such case, the SO comprises in a 5' to 3' direction (i) a 5'-tagging portion comprising a non-complementary sequence to the extended strand and (ii) a 3'-hybridization portion comprising a non-complementary sequence to the extended strand.

Where the 5'-tagging portion of the SO comprises a nucleotide sequence complementary to the CTO (e.g., the capturing portion of CTO), the cleavage of the SO of the extended strand/SO hybrid by a 5' nuclease, a ribonuclease or a restriction enzyme releases a fragment comprising the 5'-tagging portion or a part of the 5'-tagging portion of the SO and the fragment released from the SO is capable of hybridization with the CTO and extension. Thus, an extended strand is additionally produced.

In an embodiment of this invention, the production of the extended strand and the cleavage by a nucleolytic enzyme (particularly, a restriction enzyme) are performed in separate tubes.

Step (g): Detection of Cleavage of Extended Strand/SO Hybrid Indicating the Presence of Target Nucleic Acid Sequences Following the cleavage reaction of the extended strand/SO hybrid, the occurrence of the cleavage reaction of the extended strand/SO hybrid is detected for analysis of the presence of the target nucleic acid sequence.

According to an embodiment, the detection of the occurrence of the cleavage reaction of the extended strand/SO hybrid is carried out by detecting signal provided from the label linked to the SO.

The signaling system adopted to the present invention is characterized by direct association of the cleavage of the extended strand/SO hybrid with a signal generation. According to an embodiment, the signaling system used in the present invention causes a signal change upon the cleavage of the extended strand/SO hybrid. Since the cleavage of the extended strand/SO hybrid occurs only when the target nucleic acid sequence is present and the PTO is cleaved, the present invention provides the signal indicating the presence of the target nucleic acid sequence. If desired, the present invention is carried out in a real-time manner.

For direct association of the cleavage of the extended strand/SO hybrid with a signal generation, the present invention employs at least one label linked to the SO to provide signal.

In certain embodiment, the label system useful in this invention is an interactive label or single label.

(i) Interactive Label

The interactive label system is a signal generating system in which energy is passed non-radioactively between a donor molecule and an acceptor molecule. As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively.

According to an embodiment of this invention, the signal indicative of the occurrence of the cleavage of the extended strand/SO hybrid (i.e., the presence of the target nucleic acid sequence) is generated by interactive label systems, particularly the FRET label system (i.e., interactive dual label system).

According to an embodiment, the SO has an interactive dual label comprising a reporter molecule and a quencher molecule, the cleavage site for the nucleolytic enzyme is positioned between the reporter molecule and the quencher molecule linked to the SO, the cleavage of the SO of the extended strand/SO hybrid separates the reporter molecule and the quencher molecule from each other and the occurrence of the cleavage reaction of the SO of the extended strand/SO hybrid is detected by measuring a signal from the label.

In certain embodiment, prior to the formation of the extended strand/SO hybrid, the quencher molecule is positioned at a site suitable to quench signal from the reporter molecule.

The interactive label system in the present invention is useful in a liquid phase and on a solid phase.

Where the interactive label system is employed, the cleavage site generated in the step (e) is a cleavage site for 5' nuclease, restriction enzyme or ribonuclease.

The principle underlying the interactive label system in the present invention is illustrated in FIGS. 2 to 5. The PTO fragment is release from the PTO hybridized with the target nucleic acid sequence, then hybridized with the capturing portion of the CTO and extended to form an extended strand comprising an extended sequence complementary to the templating portion of the CTO. The SO is hybridized with the extended strand and cleaved by a nucleolytic enzyme. At this time, the reporter molecule and the quencher molecule linked to the SO are separated from each other and quenching by the quencher molecule is prevented to induce a signal change (e.g., signal increase from reporter molecule), finally providing a detectable signal.

The dual label on the SO may be positioned such that unquenching occurs upon hybridization of the SO with the extended strand. The separation of the reporter and the quencher from each other on the SO by the successive cleavage reaction may result in complete relief of quenching. The signal from the labeled fragment is then measured to detect the occurrence of the cleavage reaction.

In the absence of the target nucleic acid sequence, the PTO is not cleaved and the uncleaved PTO is not extended while it is hybridized with the capturing portion of the CTO. In such case, the reporter molecule and the quencher molecule linked to the non-hybridized SO are adjacent to each other to allow the quencher molecule to quench signal from the reporter molecule.

The target nucleic acid sequence may be detected according to the principle described above.

Prior to the formation of the extended strand/SO hybrid, the quencher molecule is positioned at a site suitable to quench signal from the reporter molecule. In certain embodiment, the reporter molecule and the quencher molecule are adjacent to each other along the length of the SO or adjacent to each other by formation of a conformational structure of the SO such as random coil and hairpin structure.

The nucleolytic enzyme (e.g., 5' nuclease) may cleave a 5'-end portion of the SO of the extended strand/SO hybrid to release the reporter molecule, thereby inducing signal change from the reporter molecule. The occurrence of the cleavage of the extended strand/SO hybrid may be detected by measuring the fluorescent signal for determination of the presence of the target nucleic acid sequence.

Where the quencher molecule is fluorescent, the occurrence of the cleavage of the extended strand/SO hybrid may be detected by measuring signal from the fluorescent quencher.

According to an embodiment, at least one of the reporter molecule and the quencher molecule is linked to the 5'-end of the SO. In certain embodiment, one of the reporter molecule and the quencher molecule is linked to the 5'-end of the SO and the other to the 3'-end.

According to an embodiment, one of the reporter molecule and the quencher molecule on the SO is located at its 5'-end or at 1-10 nucleotides apart from its 5'-end and the other is located to quench the signal from the reporter molecule before the hybridization of SO with the extended strand.

According to an embodiment, one of the reporter molecule and the quencher molecule on the SO is located at its 3'-end or at 1-10 nucleotides apart from its 3'-end and the other is located to quench and the signal from the reporter molecule before the hybridization of SO with the extended strand.

For instance, the reporter molecule on the SO may be located at the 5'-end or at 1-5 nucleotides apart from its 5'-end and the quencher molecule may be located at 5-80 nucleotides apart from the reporter molecule.

According to an embodiment, the interactive dual label is located at sites sufficient to maintain quenching phenomenon prior to the formation of the extended strand/SO hybrid, and induce unquenching upon the cleavage of the extended strand/SO hybrid.

Considering real-time signal generation during the cleavage of the extended strand/SO hybrid, the reporter molecule and the quencher molecule may be positioned at no more than 80 nucleotides, no more than 60 nucleotides, no more than 30 nucleotides, no more than 25 nucleotides, no more than 20 nucleotides, no more than 15 nucleotides, or no more than 10 nucleotides apart from each other. According to an embodiment, the reporter molecule and the quencher molecule may be separated by at least 3 nucleotides, at least 4 nucleotides, at least 5 nucleotides, at least 6 nucleotides, at least 10 nucleotides or at least 15 nucleotides.

Furthermore, because the cleaved fragment having a label (e.g., reporter molecule) is produced, the occurrence of the cleavage of the extended strand/SO hybrid may be analyzed by directly detecting a signal from the label linked to the cleaved fragment under more flexible or convenient conditions (e.g., high-stringent conditions or conditions after washing on a solid substrate).

According to an embodiment, one of the interactive dual label linked to the immobilized SO is remained on the solid substrate after the cleavage of the extended strand/SO hybrid.

According to an embodiment, where the SO immobilized onto the solid substrate has the interactive dual label and 5' nuclease is used as nucleolytic enzymes, one of the interactive dual label may be securely remained on the solid substrate after the cleavage of the extended strand/SO hybrid by conferring suitable conditions for dissociating a fragment of the SO from the hybrid or conferring resistance to 5' nuclease activities into internal nucleotides of the SO (e.g., nucleotides having a backbone resistant to the 5' to 3' exonuclease activity or nucleotides having a label on its base).

According to an embodiment, the resistance to 5' nuclease activities is conferred by nucleotides having a backbone resistant to the 5' to 3' exonuclease activity, including various phosphorothioate linkages, phosphonate linkages, phosphoroamidate linkages and 2'-carbohydrates modifications, particularly, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-(3-β-ribofuranosyl) modification.

Where the SO comprises the 5'-tagging portion non-complementary to the extended strand, either reporter or quencher molecule may be positioned on the 5'-tagging portion considering the cleavage site.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red(615), Nile Red (628), YO-PRO™-3 (631), YOYO™-3 (631), R-phycocyanin (642), C-Phycocyanin (648), TO-PRO™-3 (660), TOTO3 (660), DiD DiIC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. For example, the reporter molecule and the quencher molecule include JOE, FAM, TAMRA, ROX and fluorescein-based label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, 2$^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, 6$^{th}$ Edition (Molecular Probes, Eugene, Oreg., 1996) U.S. Pat. Nos. 3,996,345 and 4,351,760.

It is noteworthy that a non-fluorescent black quencher molecule (or dark quencher molecule) capable of quenching a fluorescence of a wide range of wavelengths or a specific wavelength may be used in the present invention. Examples of those are BHQ and DABCYL.

In the FRET label adopted to the SO, the reporter encompasses a donor of FRET and the quencher encompasses the other partner (acceptor) of FRET. For example, a fluorescein dye is used as the reporter and a rhodamine dye as the quencher.

The labels may be linked to the SO by conventional methods. For instance, the labels are linked to the SO through a spacer containing carbon atoms (e.g., 3-carbon spacer, 6-carbon spacer or 12-carbon spacer).

(ii) Single Label

The present invention is also excellently executed using single label systems for providing signals for the occurrence of the extended strand/SO hybrid indicating the presence of target nucleic acid sequences.

The single label includes, but not limited to, a fluorescent label, a luminescent label, a chemiluminescent label, an electrochemical label and a metal label. Particularly, the single label includes a fluorescent label.

There are single labels showing different signals depending on whether they are linked to or released from oligonucleotides or whether they are linked to an intact oligonucleotide or to a fragment of the oligonucleotide. When such single labels are used, the present invention may give a signaling system synchronized with the cleavage of the extended strand/SO hybrid even in a liquid phase. For example, a fluorescent terbium chelate provides different signals depending on whether it is linked to or released from oligonucleotides (Nurmi et al, Nucleic Acids Research, 2000, Vol. 28 No. 8 e28). For another example, where the single label is a dye emitting a polarized fluorescence through excitation by plane polarized light, the cleaved fragment containing the single label may be detected by a fluorescence polarization (FP) method. The extent of the polarization of the emitted fluorescence is affected by motion of molecules linked to the label. Generally, as the motion becomes faster, the extent of the polarization becomes lower (Latif et al, Genome Research, 11:436-440, 2001).

In certain embodiment, the single label capable of generating differential signals depending on the cleavage of the extended strand/SO hybrid is a fluorescent terbium chelate or a dye emitting a polarized fluorescence.

Where a signaling system used is designed such that a fragment produced in cleavage of the SO contains a single label, the occurrence of the cleavage of the extended strand/SO hybrid is effectively detected by using the labeled fragment. In certain embodiment, the occurrence of the cleavage of the extended strand/SO hybrid is conveniently analyzed by detection of the labeled fragment on electrophoresis.

In an embodiment of the present invention, the SO has a single label, the cleavage of the SO of the extended strand/SO hybrid produces a fragment having the single label, and the occurrence of the cleavage of the SO of the extended strand/SO hybrid is detected by detecting the release of the single-labeled fragment. In such case, a signal from the single label prior to the cleavage of the SO is different from a signal from the single label after the cleavage of the SO, and the difference in signals allows to detect the occurrence of the cleavage of the SO of the extended strand/SO hybrid.

According to an embodiment, the single label is linked to the 5'-end or the 3'-end of the SO.

Where the present invention uses the single label, the present invention is efficiently performed on a solid phase using immobilized SOs. According to an embodiment, the SO is immobilized through its 5'-end or its 3'-end onto a solid substrate.

According to an embodiment, the SO is immobilized on the surface of a solid substrate via its 3'-end or 5'-end, the SO has a single label, the cleavage of the SO of the extended strand/SO hybrid produces a fragment having the single label, and the fragment is released on the solid substrate, whereby a signal change occurs on the solid substrate to detect the occurrence of the cleavage of the SO of the extended strand/SO hybrid.

Where the SO is immobilized through its 3'-end onto the solid substrate, the single label is linked to the 5'-end of the SO and the cleavage site generated in the step (e) is that for 5' nuclease, restriction enzyme or ribonuclease.

As illustrated in FIG. 6, the extended strand of the PTO fragment is hybridized with the SO immobilized through its 3'-end onto a solid substrate to generate the cleavage site for 5' nuclease. The 5' nuclease cleaves the extended strand/SO hybrid by attacking the cleavage site and releases a fluorescent reporter molecule from the 5'-end of the SO. Where the target nucleic acid sequence is present, spots containing immobilized SOs are observed to show decrease or extinguishment of fluorescence. In the absence of the target nucleic acid sequence, the decrease or extinguishment of fluorescence in spots containing immobilized SOs are not observed.

In particular, where the present invention on a solid phase is performed using a single label, it can utilize a general fluorescent label and does not require a specific fluorescent label capable of providing a fluorescent signal with different intensities depending on whether it is linked to or released from oligonucleotides or whether it is linked to an intact oligonucleotide or to a fragment of the oligonucleotide. In the present invention on the solid phase, the differential signals depending on the occurrence of the cleavage of the extended strand/SO hybrid may be analyzed even by detection of the remaining of the single label on the solid phase. In this regard, the workability of the single label in the present invention becomes highlighted on the solid phase.

As described above, the presence or absence of signal, or the signal change (increase or decrease in signal intensity) provided by the single label in a synchronized manner with the second cleavage reaction is measured to detect the presence of the target nucleic acid sequence.

Examples of the single fluorescent label useful in the present invention may be described with reference to descriptions for reporter and quencher molecules as indicated above.

The single label may be linked to the SO by conventional methods. For instance, the single label is linked to the SO through a spacer containing carbon atoms (e.g., 3-carbon spacer, 6-carbon spacer or 12-carbon spacer).

In certain embodiment, the single label on the SO is located at the 5'-end or at 1-5 nucleotides apart from the 5'-end. Alternatively, the single label is located at the 3'-end or at 1-5 nucleotides apart from the 3'-end of the SO.

The primer, PTO, CTO and SO may be comprised of naturally occurring dNMPs. Alternatively, the primer, PTO, CTO and SO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PTO and CTO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

As described above, the PTO may be cleaved at a site located in a 3'-direction apart from the 3'-end of the 5'-tagging portion of the PTO. The cleavage site may be located at the 5'-end part of the 3'-targeting portion of the PTO. Where the PTO fragment comprises the 5'-end part of the 3'-targeting portion of the PTO, a site of the CTO hybridized with the 5'-end part of the 3'-targeting portion may comprise a universal base, degenerate sequence or their combination. For instance, if the PTO is cleaved at a site located one nucleotide in a 3'-direction apart from the 3'-end of the 5'-tagging portion of the PTO, it is advantageous that the 5'-end part of the capturing portion of the CTO comprises a universal base for hybridization with the nucleotide. If the PTO is cleaved at a site located two nucleotides in a 3'-direction apart from the 3'-end of the 5'-tagging portion of the PTO, it is advantageous that the 5'-end of the capturing portion of the CTO comprises a degenerate sequence and its 3'-direction-adjacent nucleotide comprises a universal base. As such, where the cleavage of the PTO occurs at various sites of the 5'-end part of the 3'-targeting portion, the utilization of universal bases and degenerate sequences in the CTO is useful. In addition, where the PTOs having the same 5'-tagging portion are used for screening multiple target nucleic acid sequences under upstream primer extension-dependent cleavage induction, the PTO fragments having different 5'-end parts of the 3'-targeting portion may be generated. In such cases, universal bases and degenerate sequences are usefully employed in the CTO. The strategies using universal bases and degenerate sequences in the CTO ensure to use one type or minimal types of the CTO for screening multiple target nucleic acid sequences.

According to an embodiment, the present method further comprises repeating all or some of the steps (a)-(g) with denaturation between repeating cycles. This repetition permits to amplify the target nucleic acid sequence and/or the target signal. The denaturation may be carried out by conventional technologies, including, but not limited to, heating, alkali, formamide, urea and glycoxal treatment, enzymatic methods (e.g., helicase action), and binding proteins. For instance, the melting can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

According to an embodiment, the steps (a)-(b), (a)-(d), (a)-(e), (a)-(f) or (a)-(g) may be repeated with denaturation.

It would be appreciated by one of skill in the art that the repetition of the steps (a)-(f) is an embodiment for generation of the fragment of the SO and its variations may be performed. For instance, the present invention may be carried out by repeating the steps (a)-(b), performing the steps (c)-(f) to generate the fragment of the SO, and detecting the fragment of the SO.

According to an embodiment, the steps (a)-(g) are performed in a single reaction vessel or some of the steps (a)-(g) are performed in separate vessels. For example, the steps (a)-(b), (c)-(d) or (e)-(f) may be performed in a single reaction vessel or separate reaction vessels. For example, where the sequences of the PTO and CTO, and the reaction conditions are determined such that the hybridization between the 3'-targeting portion of the PTO and the target nucleic acid sequence may be performed under higher stringent conditions than the hybridization between the PTO fragment and the CTO, the steps (a)-(b) may be repeated with no undertaking the steps (c)-(g). Following the repetition of the steps (a)-(b), the steps (c)-(g) may be performed.

According to an embodiment, the steps (a)-(b) may be repeated with denaturation.

It would be appreciated by one of skill in the art that repetition of certain steps, intervention of denaturation in repetition, separate performance of certain step(s) and time point of detection may be widely varied.

According to an embodiment, where the repetition is performed with denaturation using the upstream primer to the PTO, the repetition is carried out in the presence of a downstream primer, particularly according to PCR. The use of the upstream primer and downstream primer to the PTO can amplify the target nucleic acid sequence.

According to an embodiment, where the repetition is performed with denaturation using the upstream probe to the PTO, the repetition is carried out in the presence of a downstream primer to the PTO.

The present invention does not require that target nucleic acid sequences to be detected and/or amplified have any particular sequence or length, including any DNA (gDNA and cDNA) and RNA molecules. The target nucleic acid sequence may be in a single- or double-strand.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligonucleotide dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The target nucleic acid sequence to be detected by the present invention includes a wide variety of nucleic acid sequences, e.g., sequences in a genome, artificially isolated or fragmented sequences and synthesized sequences (e.g., cDNA sequences and barcode sequences). For instance, the target nucleic acid sequence includes nucleic acid marker sequences for Immuno-PCR (IPCR). IPCR employs conjugates between nucleic acid marker sequences and antibodies together with PCR, which is widely applied for detecting various types of targets including proteins (see Sano et al., Science 258 pp:120-122(1992), U.S. Pat. No. 5,665,539, Niemeyer et al., Trends in Biotechnology 23 pp:208-216 (2005), U.S. Pat. Pub. No. 2005/0239108 and Ye et al., Journal of Environmental Science 22 pp:796-800(2010)).

The present invention is also useful in detection of a nucleotide variation. Preferably, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic acid sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence. According to an embodiment, the 3'-end of the upstream primer has a complementary sequence to the nucleotide variation in a target nucleic acid sequence. The 3'-end of the upstream primer having a complementary sequence to the nucleotide variation in the target nucleic acid sequence is annealed to the matching template and extended to induce cleavage of the PTO. The resultant PTO fragment is hybridized with the CTO to provide the target signal. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no generation of the target signal.

Alternatively, it is possible to use PTO cleavage depending on the hybridization of PTO having a complementary sequence to a nucleotide variation in a target nucleic acid sequence. For example, under controlled conditions, a PTO having a complementary sequence to the nucleotide variation in the target nucleic acid sequence is hybridized with the matching template and then cleaved. The resultant PTO fragment is hybridized with the CTO to provide the target signal. While, under the controlled conditions, the PTO is not hybridized with a mismatching template having non-complementary sequence in the nucleotide variation position and not cleaved. Preferably, in this case, the complementary sequence to the nucleotide variation in the PTO is positioned at its middle of the 3'-targeting portion of the PTO.

According to an embodiment, the use of an artificial mismatch nucleotide enhances discrimination potential of the PTO to nucleotide variations.

Alternatively, the present invention uses the PTO having the nucleotide variation discrimination site positioned on the 5'-end part of the 3'-targeting portion for selectivity of the PTO to a specific nucleotide variation. The 5'-end part of the 3'-targeting portion of the PTO is positioned to a nucleotide variation in a target nucleic acid sequence for the detection of the nucleotide variation and the 5'-end part of the 3'-targeting portion of the PTO has a complementary sequence to the nucleotide variation in a target nucleic acid sequence.

Where the PTO is hybridized with the target nucleic acid sequence (i.e., match template) having the nucleotide variation complementary to the nucleotide variation discrimination site, the 5'-end part of the 3'-targeting portion forms a double strand with the match template; however, where the PTO is hybridized with a target nucleic acid sequence (i.e., mismatch template) having a nucleotide variation non-complementary to the nucleotide variation discrimination site, the 5'-end part of the 3'-targeting portion does not form a double strand with the mismatch template.

The term used herein "nucleotide variation discrimination site" with reference to the PTO is a complementary sequence on the 5'-end part of the 3'-targeting portion of the PTO to a nucleotide variation in a target nucleic acid sequence.

It is noteworthy that such distinct hybridization patterns on the nucleotide variation of interest are responsible for differences in initial cleavage sites of the PTO, thereby producing two types of PTO fragments to give signal differentiation depending on the presence of the nucleotide variation of interest.

In the presence of the nucleotide variation of interest, a first fragment is generated by cleavage of hybrid between the PTO and matching template, and in the absence of the nucleotide variation of interest, a second fragment is generate by cleavage of hybrid between the PTO and mismatching template. The second fragment comprises an additional 3'-end portion rendering the second fragment to be different from the first fragment.

In an embodiment for the detection of a single nucleotide variation, the 5'-end of the 3'-targeting portion of the PTO has a complementary sequence to the single nucleotide variation in a target nucleic acid sequence. As described above, the cleavage of the PTO hybridized with a matching template may be induced at a site immediately adjacent in a 3'-direction to the 5'-end of the 3'-targeting portion of the PTO, for example, under upstream primer extension-dependent cleavage induction. The 3'-end of the PTO fragment has the complementary nucleotide to the single nucleotide variation. The PTO fragment is hybridized with a CTO having a capturing portion comprising a sequence corresponding to the nucleotide variation and then extended to form the extended duplex, providing the target signal. If the same PTO is hybridized with a mismatching template having the identical sequence to the matching template except for the single nucleotide variation, the cleavage of the PTO may occur at a site two nucleotides apart in a 3'-direction from the 5'-end of the 3'-targeting portion of the PTO. The 3'-end of the PTO fragment has the further cleaved nucleotide than the complementary nucleotide to the single nucleotide variation. Where the site of the CTO hybridized with the additional-cleaved nucleotide is designed to have a non-complementary sequence to the further cleaved nucleotide, the 3'-end of the PTO fragment is not hybridized with the CTO, resulting in no extension of the PTO fragment in a controlled condition.

According to an embodiment, a cleavage site of the PTO having a complementary sequence to the nucleotide variation at its 5'-end part of the 3'-targeting portion is different depending on hybridization with a matching template or with a mismatching template, such that the PTO fragment released from either hybridization event has different sequence preferably, in its 3'-end part, more preferably, in its 3'-end.

According to an embodiment, the selection of the nucleotide sequence of CTO in consideration of the difference in 3'-end parts of the PTO fragments allows to discriminate the matching template from the mismatching template.

According to an embodiment, the production of either the PTO fragments may be distinctly detected by an extension reaction on the CTO.

According to an embodiment, the CTO has a sequence selected such that the CTO is not hybridized with the additional 3'-end portion of the second fragment to prevent the second fragment from extension when the second fragment is hybridized with the capturing portion of the CTO.

The extension of the first fragment is detected by occurrence of the cleavage of the extended duplex as described in the present invention.

According to an embodiment, the 5'-end part of the 3'-targeting portion of the PTO comprises a non-base pairing moiety located within 1-10 nucleotides (more preferably 1-5 nucleotides) apart from the nucleotide variation discrimination site.

The non-base pairing moiety prevents the 5'-end part of the 3'-targeting portion from formation of a double strand with the target nucleotide sequence when the PTO is hybridized with the target nucleic acid sequence having the nucleotide variation non-complementary to the variation discrimination site.

The use of the non-base pairing moiety (e.g., artificial mismatch nucleotide) enhances discrimination potential of the PTO to nucleotide variations.

According to an embodiment, the non-base pairing moiety does not inhibit the formation of a double strand between the 5'-end part and the target nucleic acid sequence when the PTO is hybridized with the target nucleic acid sequence having the nucleotide variation complementary to the nucleotide variation discrimination site.

According to an embodiment, the non-base pairing moiety widens the distance between the initial cleavage site on the hybrid of the PTO and the matching template and the initial cleavage site on the hybrid of the PTO and the mismatching template.

According to an embodiment, the introduction of a non-base paring moiety sequence enables the initial cleavage site to be adjusted, particularly the initial cleavage site on the hybrid of the PTO and the mismatching template.

According to an embodiment, the non-base pairing moiety is located downstream of the nucleotide variation discrimination site.

The non-base pairing moiety includes any moieties not forming a base pair between target nucleic acid sequences. Preferably, the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties. Universal bases as non-base pairing moieties are useful in adjusting cleavage sites of the PTO.

As base pairs containing universal bases such as deoxyinosine, 1-(2'-deoxy-beta-D-ribofuranosyl)-3-nitropyrrole and 5-nitroindole have a lower binding strength than those between natural bases, universal bases may be employed as non-base pairing moieties under certain hybridization conditions.

The non-base pairing moiety introduced into the 5'-end part has preferably 1-10, more preferably 1-5, still more preferably 1-2 moieties. A plurality of non-base pairing moieties in the 5'-end part may be present in a consecutive or intermittent manner. Preferably, the non-base pairing moiety has 2-5 consecutive moieties.

Preferably, the non-base pairing moiety is a non-base pairing chemical compound.

According to an embodiment, the nucleotide variation discrimination site and the non-base pairing moiety of the PTO are located within 10 nucleotides (more preferably 8 nucleotides, 7 nucleotides, 6 nucleotides, 5 nucleotides, 4 nucleotides, 3 nucleotides, 2 nucleotides or 1 nucleotide, still more preferably 1 nucleotide) apart from the 5'-end of the 3'-targeting portion.

According to an embodiment, the PTO has a blocker portion containing as a blocker at least one nucleotide resistant to cleavage by the enzyme having 5' nuclease activity and the blocker portion is positioned to control the initial cleavage site or prevent the cleavage at a site or sites.

For improving detection efficiency of nucleotide variations, the present invention may be performed with the PCR clamping method. The representative PCR clamping method using PNA is disclosed in Henrik et al., *Nucleic Acid Research* 21:5332-5336(1993) and Luo et al., *Nucleic Acid Research* Vol. 34, No 2 e12 (2006). For instance, the PCR clamping technology using PNA allows to amplify a nucleic acid sequence having a mutant type nucleotide variation but not to amplify a nucleic acid sequence having a wild type nucleotide variation, which is followed by the PTOCE assay, enabling more efficient detection of nucleotide variations. In particular, since the PCR clamping technology permits to amplify only a nucleic acid sequence having a specific-typed nucleotide variation, its combination with the present method would allow for minority-variant detection in a more efficient manner.

Where a probe having at its 5'-end portion a nucleotide variation discrimination portion is hybridized with a mismatch temple, its 5'-end portion may form a single strand under a certain condition. The probe may correspond to a PTO. The signal may be generated by PTO assay of the present invention. This approach may be useful in detection of a target nucleic acid sequence having a nucleotide variation non-complementary to the nucleotide variation discrimination site of probes.

According to an embodiment, the target nucleic acid sequence used in the present invention is a pre-amplified nucleic acid sequence. The utilization of the pre-amplified nucleic acid sequence permits to significantly increase the sensitivity and specificity of target detection of the present invention.

According to a preferred an embodiment, the method is performed in the presence of a downstream primer to the PTO.

The advantages of the present invention may be highlighted in the simultaneous (multiplex) detection of at least two target nucleic acid sequences.

According to an embodiment, the method is performed to detect at least two types (more preferably, at least three types, still more preferably at least five types) of target nucleic acid sequences.

According to an embodiment, the method is performed to detect at least two types (more preferably, at least three types, still more preferably at least five types) of target nucleic acid sequences; wherein the upstream oligonucleotide comprises at least two types (more preferably at least three types, still more preferably at least five types) of oligonucleotides, the PTO comprises at least two types (more preferably at least three types, still more preferably at least five types) of the PTOs, the CTO comprises at least two types (preferably at least three types, more preferably at least five types) of the CTO and the SO comprises at least two types (preferably at least three types, more preferably at least five types) of the SOs.

In certain embodiment, when the at least two types of target nucleic acid sequences are present, their corresponding at least two types of signals are provided.

Where the upstream oligonucleotide to the SO is used in the method for detecting at least two target nucleic acid sequences, it comprises at least two types upstream oligonucleotide to the SO.

According to an embodiment, the present invention is performed using at least two types of downstream primers to the PTO.

The present invention may be carried out either in a liquid phase or on a solid phase.

Target Detection Using Immobilized SO on a Solid Phase

According to an embodiment, the present invention is performed on the solid phase and the SO is immobilized through its 5'-end or 3'-end onto a solid substrate (see FIG. 6). On a solid phase, the target signal provided on the solid substrate is measured.

For the solid phase reaction, the SO is immobilized directly or indirectly (preferably indirectly) through its 5'-end or 3'-end (particularly the 3'-end) onto the surface of the solid substrate. Furthermore, the SO may be immobilized on the surface of the solid substrate in a covalent or non-covalent manner. Where the immobilized SOs are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for SO immobilization. In addition, poly (T) tail or poly (A) tail may serve as linkers.

According to an embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized CTOs on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, $Si/SiO_2$ wafer, germanium, gallium arsenide, carbon, carbon nanotube, polymers (e.g., polystyrene, polyethylene, polypropylene and polyacrylamide), sepharose, agarose and colloids. A plurality of immobilized SOs in this invention may be immobilized on an addressable region or two or more addressable regions on a solid substrate that may comprise 2-1,000,000 addressable regions. Immobilized CTOs may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because the labels on the SOs immobilized are physically separated. In this regard, the number of target nucleic acid sequences to be detected by the present invention on the solid phase is not limited.

According to an embodiment, the SO is immobilized on the surface of a solid substrate via its 3'-end or 5'-end, the SO has a single label, the cleavage of the SO of the extended strand/SO hybrid produces a fragment having the single label, and the fragment is released on the solid substrate, whereby a signal change occurs on the solid substrate to detect the occurrence of the cleavage of the SO of the extended strand/SO hybrid.

Using confocal detection devices, the signal only on the solid substrate may be detected without influence of labels suspended in a liquid phase.

The present invention using the immobilized SO may be in a single reaction vessel for hybridization, cleavage reaction and amplification, permitting providing signal changes upon target amplification in a real-time manner. Alternatively, where the cleavage reaction of the immobilized SO is performed in a separate vessel, time-dependent signal changes on a solid phase may be detected in a real-time manner.

An Embodiment with Amplification of a Target Nucleic Acid Sequence

The present invention may be carried out simultaneously with amplification of a target nucleic acid sequence using a primer pair composed of an upstream primer and a downstream primer capable of synthesizing the target nucleic acid sequence.

In another aspect of this invention, there is provided a method for detecting a target nucleic acid sequence from a DNA or a mixture of nucleic acids by a PCE-SC (PTO Cleavage and Extension-Dependent Signaling Oligonucleotide Cleavage) assay, comprising:

(a) hybridizing the target nucleic acid sequence with a primer pair comprising an upstream primer and a downstream primer and a PTO (Probing and Tagging Oligonucleotide); wherein each of the upstream primer and the downstream primer comprise a hybridizing nucleotide sequence complementary to the target nucleic acid sequences; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the PTO is located between the upstream primer and the downstream primer; wherein the PTO is blocked at its 3'-end to prohibit its extension;

(b) contacting the resultant of the step (a) to an enzyme having a 5'-nuclease activity under conditions for cleavage of the PTO; wherein the upstream primer or its extended strand induces cleavage of the PTO by the enzyme having a 5'-nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a template portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase, wherein the fragment hybridized with the capturing portion of the CTO is extended to form an extended strand comprising an extended sequence complementary to the templating portion of the CTO, thereby forming an extended duplex;

(e) hybridizing the extended strand with SO (Signaling Oligonucleotide) to form an extended strand/SO hybrid; wherein the SO comprises a complementary sequence to the extended strand and at least one label;

(f) cleaving the SO of the extended strand/SO hybrid using a nucleolytic enzyme to generate a cleaved fragment of the SO; and (g) detecting the occurrence of the cleavage reaction in the step (f); wherein the detection is performed by measuring a signal provided from the label linked to the SO, whereby the occurrence of the cleavage reaction of the SO of the extended strand/SO hybrid indicates the presence of the target nucleic acid sequence.

Since the embodiment of the present invention follows the steps of the present method described above, the common descriptions between them are omitted in order to avoid undue redundancy leading to the complexity of this specification.

According to an embodiment, the method further comprise repeating all or some of the steps (a)-(g) with denaturation between repeating cycles. The reaction repetition is accompanied with amplification of the target nucleic acid sequence. Particularly, the amplification is performed in accordance with PCR (polymerase chain reaction) which is disclosed in U.S. Pat. Nos. 4,683,195, 4,683,202, and 4,800,159.

According to an embodiment, the method is performed to detect at least two types of target nucleic acid sequences.

II. Target Nucleic Acid Detection by a PCE-SC Assay Based on Upstream Oligonucleotide-Independent 5' Nuclease Activity.

In a further aspect of the present invention, there is provided a method for detecting a target nucleic acid sequence from a DNA or a mixture of nucleic acids by a PCE-SC (PTO Cleavage and Extension-Dependent Signaling Oligonucleotide Cleavage) assay, comprising:

(a) hybridizing the target nucleic acid sequence with a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence;

(b) contacting the resultant of the step (a) to an enzyme having a 5'-nuclease activity under conditions for cleavage of the PTO; wherein the PTO is cleaved by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase, wherein the fragment hybridized with the capturing portion of the CTO is extended to form an extended strand comprising an extended sequence complementary to the templating portion of the CTO, thereby forming an extended duplex;

(e) hybridizing the extended strand with SO (Signaling Oligonucleotide) to form an extended strand/SO hybrid; wherein the SO comprises a hybridizing nucleotide sequence complementary to the extended strand and at least one label;

(f) cleaving the SO of the extended strand/SO hybrid using a nucleolytic enzyme to generate a cleaved fragment of the SO;

(g) detecting the occurrence of the cleavage reaction in the step (f); wherein the detection is performed by measuring a signal provided from the label linked to the SO, whereby the occurrence of the cleavage reaction of the SO of the extended strand/SO hybrid indicates the presence of the target nucleic acid sequence.

Since the present method based on upstream oligonucleotide-independent 5' nuclease activity is the same as those by the PCE-SC assay using upstream oligonucleotides except for no use of upstream oligonucleotides, the common descriptions between them are omitted in order to avoid undue redundancy leading to the complexity of this specification.

Interestingly, the present method based on upstream oligonucleotide-independent 5' nuclease activity practically provides target signals by the PCE-SC assay even no use of upstream oligonucleotides.

For the present method, conventional enzymes having upstream oligonucleotide-independent 5' nuclease activity may be used. Among template-dependent polymerases having 5' nuclease activity, there are several enzymes having upstream oligonucleotide-independent 5' nuclease activity, e.g., Taq DNA polymerase.

Considering amplification of target nucleic acid sequences and cleavage efficiency of the PTO, the PCE-SC assay of the present invention is preferably performed using upstream oligonucleotides.

Kits for Target Detection

In still another aspect of this invention, there is provided a kit for detecting a target nucleic acid sequence from a DNA or a mixture of nucleic acids by a PCE-SC (PTO Cleavage and Extension-Dependent Signaling Oligonucleotide Cleavage) assay, comprising:

(a) a probing and targeting oligonucleotide (PTO); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence;

(b) an upstream oligonucleotide; wherein the upstream oligonucleotide comprises a hybridizing nucleotide sequence complementary to the target nucleic acid sequence; the upstream oligonucleotide is located upstream of the PTO; wherein the upstream oligonucleotide or its extended strand induces cleavage of the PTO by an enzyme having a 5' nuclease activity such that the cleavage releases a fragment comprising the 5'-tagging portion or a part of the 5'-tagging portion of the PTO;

(c) a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a template portion comprising a nucleotide sequence non-complementary to the 5'-tagging portion and the 3'-targeting portion of the PTO; wherein the fragment released from the PTO is hybridized with the capturing portion of the CTO and extended to generate an extended strand comprising an extended sequence complementary to the template portion of the CTO, whereby an extended duplex is formed;

(d) a SO (Signaling Oligonucleotide) having at least one label; the SO comprises a complementary sequence to the extended strand; wherein the SO is hybridized with the extended strand to form an extended strand/SO hybrid; and (e) a nucleolytic enzyme; wherein the nucleolytic enzyme cleaves the SO of the extended strand/SO hybrid.

Since the kit of this invention is constructed to perform the detection method of the present invention described above, the common descriptions between them are omitted in order to avoid undue redundancy leading to the complexity of this specification.

In an embodiment of this invention, the SO comprises a hybridizable sequence to the extended sequence.

In an embodiment of this invention, the nucleolytic enzyme is a 5' nuclease and the formation of the extended strand/SO hybrid produces a cleavage site for the 5' nuclease, whereby the SO of the extended strand/SO hybrid is cleaved in a 5' to 3' direction by the 5' nuclease.

In an embodiment of this invention, the nucleolytic enzyme is a 5' nuclease and the kit further comprises an upstream oligonucleotide located upstream of the SO, such that the SO of the extended strand/SO hybrid is cleaved by the nucleolytic activity of the 5' nuclease dependent on the upstream oligonucleotide or its extended strand.

In an embodiment of this invention, the upstream oligonucleotide is an upstream primer or an upstream probe.

In an embodiment of this invention, the nucleolytic enzyme is a ribonuclease, the SO comprises a RNA sequence and the formation of the extended strand/SO hybrid produces a DNA-RNA hybrid duplex, whereby the SO of the extended strand/SO hybrid is cleaved by the ribonuclease.

In an embodiment of this invention, the nucleolytic enzyme is a restriction enzyme, the SO comprises a sequence recognized by the restriction enzyme and the SO of the extended strand/SO hybrid is cleaved by the restriction enzyme.

In an embodiment of this invention, the formation of the extended strand/SO hybrid produces a cleavage site for a nucleolytic enzyme capable of cleaving a DNA duplex, a RNA duplex or a DNA-RNA hybrid duplex.

In an embodiment of this invention, the nucleolytic enzyme is a 5' nuclease and the 5' nuclease is a template-dependent DNA polymerase having a 5' nuclease activity or FEN nuclease.

In an embodiment of this invention, the SO has an interactive dual label comprising a reporter molecule and a quencher molecule, the cleavage site for the nucleolytic enzyme is positioned between the reporter molecule and the quencher molecule linked to the SO, the cleavage of the SO of the extended strand/SO hybrid separates the reporter molecule and the quencher molecule from each other.

In an embodiment of this invention, the SO has a single label, the cleavage of the SO of the extended strand/SO hybrid produces a fragment having the single label, and the occurrence of the cleavage of the SO of the extended strand/SO hybrid is detected by detecting the release of the single-labeled fragment.

In an embodiment of this invention, the single label is a fluorescent label.

In an embodiment of this invention, the SO comprises a 5'-tagging portion comprising in its 5'-direction a non-complementary sequence to the extended strand.

In an embodiment of this invention, at least one label linked to the SO is linked to the 5'-tagging portion of the SO.

In an embodiment of this invention, the PTO, CTO and/or SO is blocked at its 3'-end to prohibit its extension.

In an embodiment of this invention, the upstream oligonucleotide is an upstream primer or an upstream probe.

In an embodiment of this invention, the kit further comprises an enzyme having a 5' nuclease activity for cleaved the PTO hybridized with the target nucleic acid sequence.

In an embodiment of this invention, the SO is immobilized on the surface of a solid substrate via its 3'-end or 5'-end and the SO has a single label.

In an embodiment of this invention, the kit is used to detect at least two types of target nucleic acid sequences; wherein the upstream oligonucleotide comprises at least two types of oligonucleotides, the PTO comprises at least two types of the PTOs, the CTO comprises at least two types of the CTOs and the SO comprises at least two types of the SOs.

In an embodiment of this invention, the upstream oligonucleotide is an upstream primer and the kit further comprises a template-dependent nucleic acid polymerase for the extension of the upstream primer.

In an embodiment of this invention, the kit further comprises a downstream primer.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

The features and advantages of this invention will be summarized as follows:

(a) The present invention does not use probes to be hybridized with target nucleic acid sequences for providing target signals. The present invention is carried out in such a manner that the extended strand is produced on the CTO having arbitrary sequences as templates depending on the presence of target nucleic acid sequences and in turn the SO as probes is hybridized with the extended strand and cleaved to give signal. The present invention employs a series of reactions including PTO hybridization and cleavage, CTO hybridization and extension, and SO hybridization and cleavage, which is responsible for the highly enhanced specificity of the present invention.

(b) The sequence of the SO may be selected regardless of the sequence of target nucleic acids; therefore, it is possible to generate a cleavage site for a nucleolytic enzyme of interest. Accordingly, the present invention may detect target nucleic acid sequences by adopting conventional target detection technologies using probe cleavage by nucleolytic enzymes such as 5' nuclease, RNase and restriction enzymes.

(c) Because the sequence of the SO may be selected regardless of the sequence of target nucleic acids, the conditions for signal generation may be conveniently controlled regardless of the sequence of target nucleic acids. Such features provide prominent advantages in multiple target detection because the reaction conditions for multiplex are no longer troublesome and prevent generation of false positive signals.

(d) As the present invention measures signal provided by cleavage of the extended strand/SO hybrid, it is not necessary to measure signals under conditions for maintaining hybridization between the extended strand and the SO. By generation of labeled fragments, signal from the label from the fragments may be detected at any temperature condition. Accordingly, the present invention may be performed under a wide variety of detection conditions (e.g., a wide range of temperatures).

(e) In conventional methods using probes to be directly hybridized with target nucleic acid sequences, the probes bind to target nucleic acid sequences in a competitive manner with complementary sequences. In contrast, the present invention may avoid such competitive hybridization. The present invention enables probe hybridization to become more effective because only the extended strand may be amplified using the CTO as templates, thereby obtaining effectively signals indicative of target nucleic acid sequences.

(f) It is noteworthy that the sequence of the 5'-tagging portion of PTO, the sequence of CTO and the sequence of the SO can be selected with no consideration of target nucleic acid sequences. This makes it possible to pre-design a pool of sequences for the 5'-tagging portion of PTO, the CTO and the SO. Although the 3'-targeting portion of the PTO has to be prepared with considering target nucleic acid sequences, the CTO and SO can be prepared in a ready-made fashion with no consideration or knowledge of target nucleic acid sequences.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Evaluation of PTO Cleavage and Extension-Dependent Signaling Oligonucleotide Cleavage (PCE-SC) Assay A New assay, PTO Cleavage and Extension-Dependent Signaling Oligonucleotide Cleavage (PCE-SC) assay, was evaluated for the detection of a target nucleic acid.

Taq DNA polymerase having a 5' nuclease activity was used for the extension of upstream primer, the cleavage of PTO, the extension of PTO fragment and cleavage of SO.

PTO and CTO have no label. PTO and CTO are blocked with a carbon spacer at their 3'-ends. The synthetic oligonucleotide for *Neisseria gonorrhoeae* (NG) gene was used as a target template. Signaling Oligonucleotide (SO) has a fluorescent reporter molecule (FAM) at its 5'-end and has a quencher molecule (BHQ-1) at its 3'-end.

FIG. 2 represents schematically PCE-SC assay employed in this Example.

The sequences of synthetic template, upstream primer, PTO, CTO and SO used in this Example are:

```
                                              (SEQ ID NO: 1)
NG-T 5'-AAATATGCGAAACACGCCAATGAGGGGCATGATGCTTTCTTT
TTGTTCTTGCTCGGCAGAGCGAGTGATACCGATCCATTGAAAAA-3'

(SEQ ID NO: 2)
NG-R 5'-CAATGGATCGGTATCACTCGC-3'

(SEQ ID NO: 3)
NG-PTO 5'-ACGACGGCTTGGCTGCCCCTCATTGGCGTGTTTCG
[C3 spacer]-3'
```

```
                                            (SEQ ID NO: 4)
NG-CTO 5'-GTCGTACCGAGATGCGCTTCTGATTCGTGCGCTGGATACC
CTGACGATATCCAGCCAAGCCGTCGTGCTGT[C3 spacer]-3'

(SEQ ID NO: 5)
NG-SO 5'-[FAM]TGCGCTGGATACCCTGACGATATCC[BHQ-1]-3'
(Underlined letters indicate the 5'-tagging
portion of PTO)
```

The reaction was conducted in the final volume of 20 µl containing 2 pmole of synthetic template (SEQ ID NO: 1) for NG gene, 10 pmole of upstream primer (SEQ ID NO: 2), 5 pmole of PTO (SEQ ID NO: 3), 0.5 pmole of CTO (SEQ ID NO: 4), 5 µmole of SO (SEQ ID NO: 5) and 10 µl of 2× Master Mix containing 2.5 mM MgCl$_2$, 200 µM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C., and 30 sec at 72° C. Detection of the generated signal was performed at the denaturation step (95° C.) of each cycle.

The detection at the denaturation temperature (95° C.) supports that the detected signal is provided from the labeled fragment generated by the cleavage of SO.

As shown FIG. 7, the fluorescent signal was detected in the presence of the template. No signal was detected in the absence of the template, PTO, CTO or SO.

Example 2

Evaluation of PCE-SC Assay Using Upstream Oligonucleotide-Dependent Cleavage of SO We further evaluated PCE-SC assay for the detection of a target nucleic acid sequence using upstream oligonucleotide (UO) located upstream of SO.

Taq DNA polymerase having a 5' nuclease activity was used for the extension of upstream primer, the cleavage of PTO, the extension of PTO fragment, the extension of UO and the cleavage of SO.

PTO and CTO have no label. PTO and CTO are blocked with a carbon spacer at their 3'-ends. The synthetic oligonucleotide for NG gene was used as a target template. SO has a fluorescent reporter molecule (FAM) at its 5'-end and has a quencher molecule (BHQ-1) at its 3'-end. UO is located upstream of SO and the extension product of UO induces cleavage of SO by 5' nuclease activity of the Taq DNA polymerase.

FIG. 4 represents schematically PCE-SC assay employed in this Example.

The sequences of synthetic template, upstream primer, PTO, CTO, SO and UO used in this Example are:

```
                                            (SEQ ID NO: 1)
NG-T 5'-AAATATGCGAAACACGCCAATGAGGGGCATGATGCTTTCTTT
TTGTTCTTGCTCGGCAGAGCGAGTGATACCGATCCATTGAAAAA-3'

(SEQ ID NO: 2)
NG-R 5'-CAATGGATCGGTATCACTCGC-3'

(SEQ ID NO: 3)
NG-PTO 5'-ACGACGGCTTGGCTGCCCCTCATTGGCGTGTTTCG
[C3 spacer]-3'

(SEQ ID NO: 4)
NG-CTO 5'-GTCGTACCGAGATGCGCTTCTGATTCGTGCGCTGGATAC
CCTGACGATATCCAGCCAAGCCGTCGTGCTGT[C3 spacer]-3'

(SEQ ID NO: 5)
NG-SO 5'-[FAM]TGCGCTGGATACCCTGACGATATCC[BHQ-1]-3'

(SEQ ID NO: 6)
UO 5'-TACCGAGATGCGCTTCTG-3'
(Underlined letters indicate the 5'-tagging
portion of PTO)
```

The reaction was conducted in the final volume of 20 µl containing 2 pmole of synthetic template (SEQ ID NO: 1) for NG gene, 10 pmole of upstream primer (SEQ ID NO: 2), 5 pmole of PTO (SEQ ID NO: 3), 0.5 pmole of CTO (SEQ ID NO: 4), 5 µmole of SO (SEQ ID NO: 5), 3 pmole of UO (SEQ ID NO: 6) and 10 µl of 2× Master Mix containing 2.5 mM MgCl$_2$, 200 µM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C., and 30 sec at 72° C. Detection of the generated signal was performed at the denaturation step (95° C.) of each cycle. The detection at the denaturation temperature (95° C.) supports that the detected signal is provided from the labeled fragment generated by the cleavage of SO.

As shown FIG. 8, the fluorescent signal was detected in the presence of the template. No signal was detected in the absence of the template.

Example 3

Evaluation of PCE-SC Assay Using Upstream Primer-Independent Cleavage of PTO We further evaluated PCE-SC assay for the detection of a target nucleic acid sequence without using upstream primer located upstream of PTO.

Taq DNA polymerase having a 5' nuclease activity was used for the cleavage of PTO, the extension of PTO fragment, the extension of UO and the cleavage of SO.

PTO and CTO have no label. PTO and CTO are blocked with a carbon spacer at their 3'-ends. The synthetic oligonucleotide for NG gene was used as a target template. SO has a fluorescent reporter molecule (FAM) at its 5'-end and has a quencher molecule (BHQ-1) at its 3'-end. In this Example, PTO is cleaved by 5' nuclease activity of Taq DNA polymerase without involvement of an upstream primer located upstream of the PTO. UO is located upstream of SO and the extension product of UO induces cleavage of SO by 5' nuclease activity of the Taq DNA polymerase.

The sequences of synthetic template, PTO, CTO, SO and UO used in this Example are:

```
                                            (SEQ ID NO: 1)
NG-T 5'-AAATATGCGAAACACGCCAATGAGGGGCATGATGCTTTCTTT
TTGTTCTTGCTCGGCAGAGCGAGTGATACCGATCCATTGAAAAA-3'

(SEQ ID NO: 3)
NG-PTO 5'-ACGACGGCTTGGCTGCCCCTCATTGGCGTGTTTCG
[C3 spacer]-3'

(SEQ ID NO: 4)
NG-CTO 5'-GTCGTACCGAGATGCGCTTCTGATTCGTGCGCTGGATACC
CTGACGATATCCAGCCAAGCCGTCGTGCTGT[C3 spacer]-3'

(SEQ ID NO: 5)
NG-SO 5'-[FAM]TGCGCTGGATACCCTGACGATATCC[BHQ-1]-3'
```

-continued

UO 5'-TACCGAGATGCGCTTCTG-3' (SEQ ID NO: 6)
(Underlined letters indicate the 5'-tagging portion of PTO)

The reaction was conducted in the final volume of 20 μl containing 2 pmole of synthetic template (SEQ ID NO: 1) for NG gene, 5 pmole of PTO (SEQ ID NO: 3), 0.5 pmole of CTO (SEQ ID NO: 4), 5 pmole of SO (SEQ ID NO: 5), 3 pmole of UO (SEQ ID NO: 6) and 10 μl of 2× Master Mix containing 2.5 mM MgCl$_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C., and 30 sec at 72° C. Detection of the generated signal was performed at the denaturation step (95° C.) of each cycle. The detection at the denaturation temperature (95° C.) supports that the detected signal is provided from the labeled fragment generated by the cleavage of SO.

As shown FIG. 9, the fluorescent signal was detected in the presence of the template. No signal was detected in the absence of the template.

Example 4

Detection of a Target Nucleic Acid Sequence Using PCE-SC Assay

We further examined whether PCE-SC assay can detect a target nucleic acid sequence.

Taq DNA polymerase having a 5' nuclease activity was used for the extension of upstream primer and downstream primer, the cleavage of PTO and the extension of PTO fragment, the extension of UO and the cleavage of SO.

PTO and CTO have no label. PTO and CTO are blocked with a carbon spacer at their 3'-ends. The genomic DNA of NG gene was used as a target template. SO has a fluorescent reporter molecule (FAM) at its 5'-end and has a quencher molecule (BHQ-1) at its 3'-end. UO is located upstream of SO and the extension product of UO induces cleavage of SO by 5' nuclease activity of the Taq DNA polymerase.

The sequences of upstream primer, downstream primer, PTO, CTO, SO and UO used in this Example are:

NG-F 5'-TACGCCTGCTACTTTCACGCT-3' (SEQ ID NO: 7)

NG-R 5'-CAATGGATCGGTATCACTCGC-3' (SEQ ID NO: 2)

NG-PTO 5'-ACGACGGCTTGGCTGCCCCTCATTGGCGTGTTTCG[C3 spacer]-3' (SEQ ID NO: 3)

NG-CTO 5'-GTCGTACCGAGATGCGCTTCTGATTCGTGCGCTGGATACCCTGACGATATCCAGCCAAGCCGTCGTGCTGT[C3 spacer]-3' (SEQ ID NO: 4)

NG-SO 5'-[FAM]TGCGCTGGATACCCTGACGATATCC[BHQ-1]-3' (SEQ ID NO: 5)

UO 5'-TACCGAGATGCGCTTCTG-3' (SEQ ID NO: 6)
(Underlined letters indicate the 5'-tagging portion of PTO)

The reaction was conducted in the final volume of 20 μl containing 100 pg of genomic DNA of NG, 10 pmole of upstream primer (SEQ ID NO: 2), 10 pmole of downstream primer (SEQ ID NO: 7), 5 pmole of PTO (SEQ ID NO: 3), 0.5 pmole of CTO (SEQ ID NO: 4), 5 pmole of SO (SEQ ID NO: 5), 3 pmole of UO (SEQ ID NO: 6) and 10 μl of 2× Master Mix containing 2.5 mM MgCl$_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 40 cycles of 30 sec at 95° C., 60 sec at 60° C., and 30 sec at 72° C. Detection of the generated signal was performed at the denaturation step (95° C.) of each cycle. The detection at the denaturation temperature (95° C.) supports that the detected signal is provided from the labeled fragment generated by the cleavage of SO.

As shown FIG. 10, the fluorescent signal was detected in the presence of the template. No signal was detected in the absence of the template.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence from a DNA or a mixture of nucleic acids by a PCE-SC (PTO Cleavage and Extension-Dependent Signaling Oligonucleotide Cleavage) assay, comprising:

(a) hybridizing the target nucleic acid sequence with an upstream oligonucleotide and a PTO (Probing and Tagging Oligonucleotide); said upstream oligonucleotide comprising a hybridizing nucleotide sequence complementary to the target nucleic acid sequence; said PTO comprising (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5'-nuclease activity under conditions for cleavage of the PTO; wherein the upstream oligonucleotide or its extended strand induces cleavage of the PTO by the enzyme having a 5'-nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a template portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase, wherein the fragment hybridized with the capturing portion of the CTO is extended to form an extended strand comprising an extended sequence complementary to the templating portion of the CTO, thereby forming an extended duplex;

(e) hybridizing the extended strand with SO (Signaling Oligonucleotide) to form an extended strand/SO hybrid; wherein the SO comprises a hybridizing nucleotide sequence complementary to the extended strand and at least one label;

(f) cleaving the SO of the extended strand/SO hybrid using a nucleolytic enzyme to generate a cleaved fragment of the SO; and (g) detecting the occurrence of the cleavage reaction in the step (f); wherein the detection is performed by measuring a signal provided from the label linked to the SO, whereby the occurrence of the cleavage reaction of the SO of the extended strand/SO hybrid indicates the presence of the target nucleic acid sequence.

2. The method according to claim 1, said SO comprising a hybridizable sequence to the extended sequence.

3. The method according to claim 1, wherein the nucleolytic enzyme is a 5' nuclease and the formation of the extended strand/SO hybrid in the step (e) produces a cleavage site for the 5' nuclease, whereby the SO of the extended strand/SO hybrid is cleaved in a 5' to 3' direction by the 5' nuclease.

4. The method according to claim 1, wherein the nucleolytic enzyme is a 5' nuclease and the step (f) is performed in the presence of an upstream oligonucleotide located upstream of the SO, such that the SO of the extended strand/SO hybrid is cleaved by the nucleolytic activity of the 5' nuclease dependent on the upstream oligonucleotide or its extended strand.

5. The method according to claim 1, wherein the nucleolytic enzyme is a ribonuclease, said SO comprising a RNA sequence and the formation of the extended strand/SO hybrid in the step (e) produces a DNA-RNA hybrid duplex, whereby the SO of the extended strand/SO hybrid is cleaved by the ribonuclease.

6. The method according to claim 1, wherein the nucleolytic enzyme is a restriction enzyme, said SO comprising a sequence recognized by the restriction enzyme and the formation of the extended strand/SO hybrid in the step (e) produces a cleavage site for the restriction enzyme, whereby the SO of the extended strand/SO hybrid is cleaved by the restriction enzyme.

7. The method according to claim 1, wherein the formation of the extended strand/SO hybrid in the step (e) produces a cleavage site for a nucleolytic enzyme capable of cleaving a DNA duplex, a RNA duplex or a DNA-RNA hybrid duplex.

8. The method according to claim 1, wherein the nucleolytic enzyme in the step (f) is a 5' nuclease and the 5' nuclease is a template-dependent DNA polymerase having a 5' nuclease activity or FEN nuclease.

9. The method according to claim 1, wherein the SO has an interactive dual label comprising a reporter molecule and a quencher molecule, the cleavage site for the nucleolytic enzyme is positioned between the reporter molecule and the quencher molecule linked to the SO, the cleavage of the SO of the extended strand/SO hybrid separates the reporter molecule and the quencher molecule from each other and the occurrence of the cleavage reaction of the SO of the extended strand/SO hybrid is detected by measuring a signal from the label.

10. The method according to claim 1, wherein the SO has a single label, the cleavage of the SO of the extended strand/SO hybrid produces a fragment having the single label, and the occurrence of the cleavage of the SO of the extended strand/SO hybrid is detected by detecting the release of the single-labeled fragment.

11. The method according to claim 1, said SO comprising a 5'-tagging portion, said 5'-tagging portion comprising in its 5'-direction a non-complementary sequence to the extended strand.

12. The method according to claim 11, wherein the cleavage of the SO of the extended strand/SO hybrid releases a fragment comprising the 5'-tagging portion or a part of the 5'-tagging portion of the SO and the fragment released from the SO is capable of hybridization with the CTO and extension.

13. The method according to claim 1, wherein the PTO, CTO and/or SO is blocked at its 3'-end to prohibit its extension.

14. The method according to claim 1, wherein the SO is immobilized on the surface of a solid substrate via its 3'-end or 5'-end, the SO has a single label, the cleavage of the SO of the extended strand/SO hybrid produces a fragment having the single label, and the fragment is released on the solid substrate, whereby a signal change occurs on the solid substrate to detect the occurrence of the cleavage of the SO of the extended strand/SO hybrid.

15. The method according to claim 1, wherein the method further comprises a denaturation step between the steps (d) and (e).

16. The method according to claim 1, wherein the method further comprises repeating all or some of the steps (a)-(g) with denaturation between repeating cycles.

17. The method according to claim 1, wherein the steps (a)-(g) are performed in a single reaction vessel or some of the steps (a)-(g) are performed in separate vessels.

18. The method according to claim 1, wherein the method is performed to detect at least two types of target nucleic acid sequences; wherein the upstream oligonucleotide comprises at least two types of oligonucleotides, the PTO comprises at least two types of the PTOs, the CTO comprises at least two types of the CTOs and the SO comprises at least two types of the SOs.

19. The method according to claim 1, wherein the target nucleic acid sequence comprises a nucleotide variation.

20. The method according to claim 1, wherein the method is performed in the presence of a downstream primer.

21. A method for detecting a target nucleic acid sequence from a DNA or a mixture of nucleic acids by a PCE-SC (PTO Cleavage and Extension-Dependent Signaling Oligonucleotide Cleavage) assay, comprising:

(a) hybridizing the target nucleic acid sequence with a primer pair comprising an upstream primer and a downstream primer and a PTO (Probing and Tagging Oligonucleotide); each of said upstream primer and said downstream primer comprising a hybridizing nucleotide sequence complementary to the target nucleic acid sequence; said PTO comprising (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the PTO is located between the upstream primer and the downstream primer; wherein the PTO is blocked at its 3'-end to prohibit its extension;

(b) contacting the resultant of the step (a) to an enzyme having a 5'-nuclease activity under conditions for cleavage of the PTO; wherein the upstream primer or its extended strand induces cleavage of the PTO by the enzyme having a 5'-nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a template portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase, wherein the fragment hybridized with the capturing portion of the CTO is extended to form an extended strand comprising an extended sequence complementary to the templating portion of the CTO, thereby forming an extended duplex;

(e) hybridizing the extended strand with SO (Signaling Oligonucleotide) to form an extended strand/SO hybrid; wherein the SO comprises a complementary sequence to the extended strand and at least one label;

(f) cleaving the SO of the extended strand/SO hybrid using a nucleolytic enzyme to generate a cleaved fragment of the SO; and (g) detecting the occurrence of the cleavage reaction in the step (f); wherein the detection is performed by measuring a signal provided from the label linked to the SO, whereby the occurrence of the cleavage reaction of the SO of the extended strand/SO hybrid indicates the presence of the target nucleic acid sequence.

22. The method according to claim 21, said method further comprising repeating all or some of the steps (a)-(g) with denaturation between repeating cycles.

* * * * *